(12) United States Patent
Greenberg et al.

(10) Patent No.: US 12,428,663 B2
(45) Date of Patent: Sep. 30, 2025

(54) IDENTIFICATION OF DNA POLYMERASE THETA INACTIVATION MECHANISM

(71) Applicant: The Johns Hopkins University, Baltimore, MD (US)

(72) Inventors: Marc Greenberg, Baltimore, MD (US); Daniel Laverty, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1148 days.

(21) Appl. No.: 17/259,032

(22) PCT Filed: Jul. 10, 2019

(86) PCT No.: PCT/US2019/041110
§ 371 (c)(1),
(2) Date: Jan. 8, 2021

(87) PCT Pub. No.: WO2020/014297
PCT Pub. Date: Jan. 16, 2020

(65) Prior Publication Data
US 2021/0340594 A1 Nov. 4, 2021

Related U.S. Application Data

(60) Provisional application No. 62/696,591, filed on Jul. 11, 2018.

(51) Int. Cl.
*C12Q 1/48* (2006.01)
*A61K 31/7048* (2006.01)

(52) U.S. Cl.
CPC ............ *C12Q 1/48* (2013.01); *A61K 31/7048* (2013.01); *G01N 2333/9126* (2013.01)

(58) Field of Classification Search
CPC .................. C12Q 1/48; A61K 31/7048; G01N 2333/9126
See application file for complete search history.

(56) References Cited

FOREIGN PATENT DOCUMENTS

| EP | 2322658 A1 | 5/2011 | | |
|---|---|---|---|---|
| WO | WO-2017070198 A1 | * | 4/2017 | ........... A61K 31/407 |

OTHER PUBLICATIONS

Paul et al. ACS Chem. Biol., 2017, 12, 1576-1583 (Year: 2017).*
Prasad et al. Nucleic Acid Research, 2009, 37, 1868-1877 (Year: 2009).*
Bebenek et al., 5'-Deoxyribose phosphate lyase activity of human DNA polymerase iota in vitro. Science. Mar. 16, 2001;291(5511):2156-9.
Belousova et al., DNA polymerases β and λ and their roles in cell. DNA Repair (Amst). May 2015;29:112-26.
Burger, Cleavage of Nucleic Acids by Bleomycin. Chem Rev. May 7, 1998;98(3):1153-1170.
Ceccaldi, R. et al., Homologous-recombination-deficient tumours are dependent on Polθ-mediated repair. Nature. Feb. 12, 2015;518(7538):258-62.
Dizdaroglu, Oxidatively induced DNA damage and its repair in cancer. Mutat Res Rev Mutat Res. Jan.-Mar. 2015;763:212-45.
Dizdaroglu et al., Mechanisms of free radical-induced damage to DNA. Free Radic Res. Apr. 2012;46(4):382-419.
Donley et al., Small Molecule Inhibitors of 8-Oxoguanine DNA Glycosylase-1 (OGG1). ACS Chem Biol. Oct. 16, 2015;10(10):2334-43.
Garcia-Diaz et al., Identification of an intrinsic 5'-deoxyribose-5-phosphate lyase activity in human DNA polymerase lambda: a possible role in base excision repair. J Biol Chem. Sep. 14, 2001;276(37):34659-63.
Goff et al., Lack of DNA polymerase theta (POLQ) radiosensitizes bone marrow stromal cells in vitro and increases reticulocyte micronuclei after total-body irradiation. Radiat Res. Aug. 2009;172(2):165-74.
Gowda et al., Honokiol Inhibits DNA Polymerases β and λ and Increases Bleomycin Sensitivity of Human Cancer Cells. Chem Res Toxicol. Feb. 20, 2017;30(2):715-725.
Greenberg, Abasic and oxidized abasic site reactivity in DNA: enzyme inhibition, cross-linking, and nucleosome catalyzed reactions. Acc Chem Res. Feb. 18, 2014;47(2):646-55.
Guan et al., Irreversible inhibition of DNA polymerase beta by an oxidized abasic lesion. J Am Chem Soc. Apr. 14, 2010;132(14):5004-5.
Higgins et al., Beyond PARP-POLθ as an anticancer target. Science. Mar. 16, 2018;359(6381):1217-1218.
Hogg et el., Lesion bypass activity of DNA polymerase θ (POLQ) is an intrinsic property of the pol domain and depends on unique sequence inserts. J Mol Biol. Jan. 21, 2011;405(3):642-52.
Jacobs et al., Long patch base excision repair compensates for DNA polymerase β inactivation by the C4'-oxidized abasic site. Biochemistry. Jan. 11, 2011;50(1):136-43.
Kim et al., Synthesis and characterization of oligonucleotides containing the c4'-oxidized abasic site produced by bleomycin and other DNA damaging agents. Angew Chem Int Ed Engl. 2003;42(47):5882-5.
Laverty et al., In Vitro Bypass of Thymidine Glycol by DNA Polymerase θ Forms Sequence-Dependent Frameshift Mutations. Biochemistry. Dec. 26, 2017;56(51):6726-6733.
Longley et al., Identification of 5'-deoxyribose phosphate lyase activity in human DNA polymerase gamma and its role in mitochondrial base excision repair in vitro. Proc Natl Acad Sci U S A. Oct. 13, 1998;95(21):12244-8.
Malaby et al., Expression and Structural Analyses of Human DNA Polymerase θ (POLQ). Methods Enzymol. 2017;592:103-121.
Matsumoto et al., Excision of deoxyribose phosphate residues by DNA polymerase beta during DNA repair. Science. Aug. 4, 1995;269(5224):699-702.
Miropolskaya et al., Identification of amino acid residues involved in the dRP-lyase activity of human Pol I. Sci Rep. Aug. 31, 2017;7(1):10194.

(Continued)

*Primary Examiner* — Thea D'Ambrosio
*Assistant Examiner* — Lioubov G Korotchkina
(74) *Attorney, Agent, or Firm* — Casimir Jones, S.C.; Robert A. Goetz

(57) ABSTRACT

Methods for identifying one or more Pol θ inhibitors and methods of use thereof are disclosed.

2 Claims, 15 Drawing Sheets

Specification includes a Sequence Listing.

(56) References Cited

OTHER PUBLICATIONS

Murai et al., Trapping of PARP1 and PARP2 by Clinical PARP Inhibitors. Cancer Res. Nov. 1, 2012;72(21):5588-99.
Muvarak et al., Enhancing the Cytotoxic Effects of PARP Inhibitors with DNA Demethylating Agents—A Potential Therapy for Cancer. Cancer Cell. Oct. 10, 2016;30(4):637-650.
Paul et al., Synergistic Effects of an Irreversible DNA Polymerase Inhibitor and DNA Damaging Agents on HeLa Cells. ACS Chem Biol. Jun. 16, 2017;12(6):1576-1583.
Prasad et al., Structural insight into the DNA polymerase beta deoxyribose phosphate lyase mechanism. DNA Repair (Amst). Dec. 8, 2005;4(12):1347-57.
Prasad et al., Functional analysis of the amino-terminal 8-kDa domain of DNA polymerase beta as revealed by site-directed mutagenesis. DNA binding and 5'-deoxyribose phosphate lyase activities. J Biol Chem. May 1, 1998;273(18):11121-6.
Prasad et al., Localization of the deoxyribose phosphate lyase active site in human DNA polymerase iota by controlled proteolysis. J Biol Chem. Aug. 8, 2003;278(32):29649-54.
Prasad et al., Human DNA polymerase theta possesses 5'-dRP lyase activity and functions in single-nucleotide base excision repair in vitro. Nucleic Acids Res. Apr. 2009;37(6):1868-77.
Prasad et al., Rev1 is a base excision repair enzyme with 5'-deoxyribose phosphate lyase activity. Nucleic Acids Res. Dec. 15, 2016;44(22):10824-10833.
Prasad et al., Substrate channeling in mammalian base excision repair pathways: passing the baton. J Biol Chem. Dec. 24, 2010;285(52):40479-88.
Rabow et al., Identification and Quantitation of the Lesion Accompanying Base Release in Bleomycin-Mediated DNA Degradation. J. Am. Chem. Soc. 1990, 112, 3196-3203.
Regulus et al., Oxidation of the sugar moiety of DNA by ionizing radiation or bleomycin could induce the formation of a cluster DNA lesion. Proc Natl Acad Sci U S A. Aug. 28, 2007;104(35):14032-7.
Sczepanski et al., Rapid DNA-protein cross-linking and strand scission by an abasic site in a nucleosome core particle. Proc Natl Acad Sci U S A. Dec. 28, 2010;107(52):22475-80.
Stevens et al., DNA polymerase $\lambda$ inactivation by oxidized abasic sites. Biochemistry. Feb. 5, 2013;52(5):975-83.
Tahara et al., Potent and Selective Inhibitors of 8-Oxoguanine DNA Glycosylase. J Am Chem Soc. Feb. 14, 2018;140(6):2105-2114.
Williams et al., Formation of a Schiff base intermediate is not required for the adenine glycosylase activity of *Escherichia coli* MutY. Biochemistry. Nov. 23, 1999;38(47):15417-24.
Wood et al., DNA polymerase $\theta$ (POLQ), double-strand break repair, and cancer. DNA Repair (Amst). Aug. 2016;44:22-32.
Wu et al., How DNA polymerases catalyse replication and repair with contrasting fidelity. Nature Rev. Chem. 2017, 1, 0068.
Yoon et al., A role for DNA polymerase $\theta$ in promoting replication through oxidative DNA lesion, thymine glycol, in human cells. J Biol Chem. May 9, 2014;289(19):13177-85.
Yoshimura et al., Vertebrate POLQ and POLbeta cooperate in base excision repair of oxidative DNA damage. Mol Cell. Oct. 6, 2006;24(1):115-25.
Yousefzadeh et al., Mechanism of suppression of chromosomal instability by DNA polymerase POLQ. PLoS Genet. Oct. 2, 2014;10(10):e1004654.
Zafar et al., Translesion DNA Synthesis in Cancer: Molecular Mechanisms and Therapeutic Opportunities. Chem Res Toxicol. Nov. 20, 2017;30(11):1942-1955.
Zafar et al., A Small-Molecule Inhibitor of Human DNA Polymerase n Potentiates the Effects of Cisplatin in Tumor Cells. Biochemistry. Feb. 20, 2018;57(7):1262-1273.
Zahn et al., Human DNA polymerase $\theta$ grasps the primer terminus to mediate DNA repair. Nat Struct Mol Biol. Apr. 2015;22(4):304-11.
International Search Report and Written Opinion for PCT/US2019/041110. Mailed Oct. 29, 2019. 11 pages.

\* cited by examiner

IDENTIFICATION OF DNA POLYMERASE THETA INACTIVATION MECHANISM

CROSS-REFERENCE TO RELATED APPLICATIONS

This application is a § 371 U.S. National Entry application of PCT/US2019/04110, filed Jul. 10, 2019, which claims the benefit of U.S. Provisional Application No. 62/696,591, filed Jul. 11, 2018, each of which is incorporated herein by reference in its entirety.

FEDERALLY SPONSORED RESEARCH OR DEVELOPMENT

This invention was made with government support under GM063028 awarded by the National Institutes of Health. The government has certain rights in the invention.

SEQUENCE LISTING

The text of the computer readable sequence listing filed herewith, titled "36635-252_SEQUENCE-_LISTING_ST25", created Jan. 8, 2021, having a file size of 3,000 bytes, is hereby incorporated by reference in its entirety.

BACKGROUND

DNA polymerase theta (Pol θ) is not essential in healthy cells, but is upregulated in breast, lung, and ovarian cancers, which correlates with a poor prognosis in the outcome of those cancers. Pol θ promotes resistance to ionizing radiation and chemotherapeutic agents, such as bleomycin. Pol θ is involved in DNA repair. Its primary activity concerns homologous recombination, a pathway involved in double-strand break repair. Pol θ also has been found to play a role in base excision repair. Like a number of DNA repair polymerases (e.g., Pol β), Pol θ is bifunctional and acts as a polymerase and a lyase.

Inhibition of Pol θ is potentially therapeutically useful, which makes Pol θ an attractive target for anticancer therapy. The potential of Pol θ as an anticancer target has been favorably compared to that of PARP1. Higgins, G. S., and Boulton, S. J. (2018). No effective Pol θ inhibitors, however, have been identified to date.

SUMMARY

In some aspects, the presently disclosed subject matter provides a method for identifying a DNA polymerase theta (Pol θ) inhibitor, the method comprising: (a) contacting Pol θ with one or more candidate Pol θ inhibitors in a Pol θ reaction buffer to form a pre-incubation mixture; (b) incubating the pre-incubation mixture for a period of time at room temperature; (c) diluting the pre-incubation mixture with a solution containing a DNA substrate and nucleotide triphosphates in a Pol θ reaction buffer; and (d) measuring fluorescence of the diluted pre-incubation mixture for a period of time. In particular aspects, the presently disclosed subject matter provides a Pol θ inhibitor, derivative or analog thereof, identified by the presently disclosed screening method.

In other aspects, the presently disclosed subject matter provides a method for inhibiting Pol θ activity in a subject, the method comprising administering to the subject a therapeutically effective amount of a Pol θ inhibitor, or an analogue or a pharmaceutically acceptable salt thereof. In particular aspects, the inhibiting is irreversible. In other aspects, the inhibiting is reversible. In certain aspects, the Pol θ inhibitor inhibits the lyase activity of Pol θ. In other aspects, the Pol θ inhibitor inhibits the polymerase activity of Pol θ. In yet more particular aspects, the Pol θ inhibitor inhibits the activity of Pol θ by modifying $Lys_{2383}$.

In other aspects, the presently disclosed subject matter provides a method for inhibiting a cancer cell, the method comprising contacting the cancer or a noncancerous cell with a Pol θ inhibitor in an amount effective to inhibit Pol θ. In certain aspects, the inhibiting of Pol θ occurs in vitro, in vivo, or ex vivo.

In yet other aspects, the presently disclosed subject matter provides a method for treating a cancer in a subject, the method comprising administering to the subject in need of treatment thereof a therapeutically effective amount of a Pol θ inhibitor, or an analogue or a pharmaceutically acceptable salt thereof. In certain aspects, the cancer is a cancer in which Pol θ is upregulated. In yet more certain aspects, the cancer is a cancer comprising one or more DNA repair defects. In particular aspects, the cancer comprising one or more DNA repair defects includes one or more BRCA-deficient cancers. In yet more particular aspects, the cancer is selected from the group consisting of breast cancer, lung cancer, and ovarian cancer.

In other aspects, the method of treating cancer further comprises administering the Pol θ inhibitor in combination with radiotherapy, one or more chemotherapeutic agents, one or more immunotherapy agents, surgery, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

Having thus described the presently disclosed subject matter in general terms, reference will now be made to the accompanying Figures, which are not necessarily drawn to scale, and wherein:

FIG. 1 shows representative kinetics plots for single turnover kinetics measuring excision by Pol θ of: (a) pC4-AP (3'-$^{32}$P-1); (b) DOB (3'-$^{32}$P-2); and (c) dRP (3'-$^{32}$P-3). Data are the average±standard deviation of three replicates;

FIG. 2A and FIG. 2B shows Pol θ inactivation by pC4-AP. FIG. 2A shows dRP, DOB, and pC4-AP excision (100 nM) by Pol θ (2.5 nM). FIG. 2B shows repeated loss of Pol θ lyase activity following addition (5 nM) to pC4-AP (100 nM). Timing of additional Pol θ aliquots indicated by arrows;

FIG. 3A and FIG. 3B show modified peptide (4) detected in tryptic digest of Pol θ (1 μM) incubated with pC4-AP (1, 10 μM). FIG. 3A is the observed spectrum (z=3); FIG. 3B is the calculated spectrum (z=3);

Figure 6:
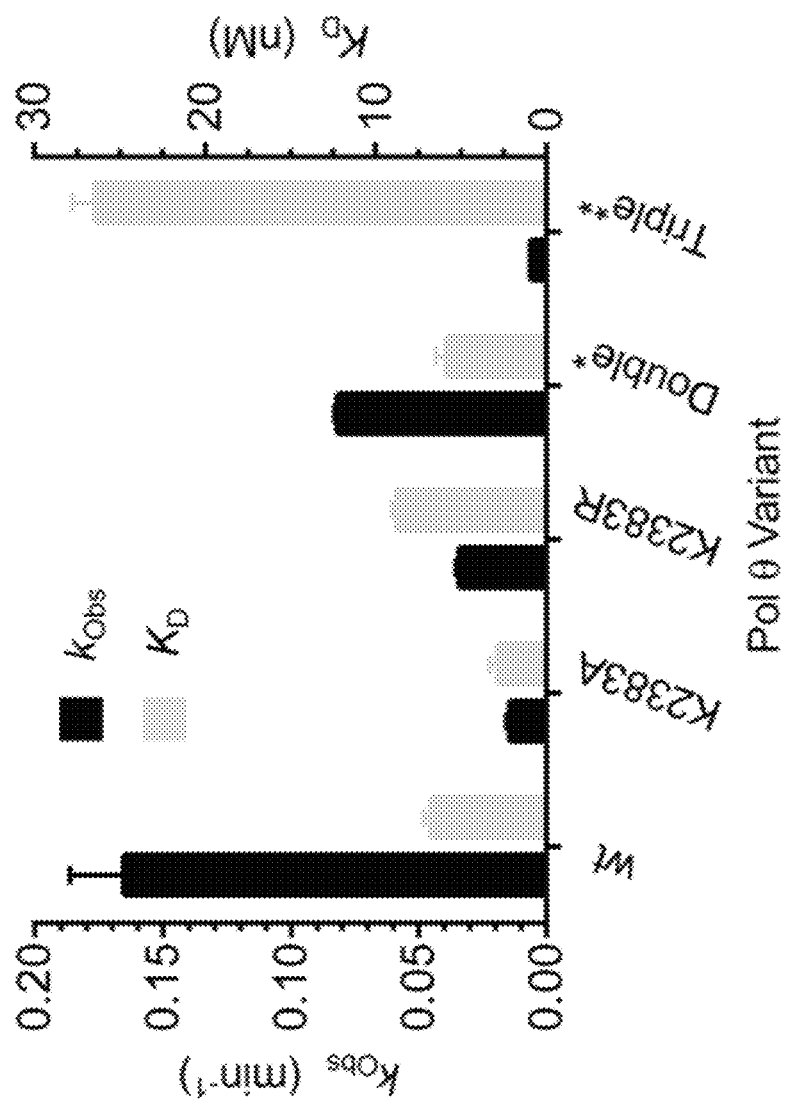
Figure 7A:
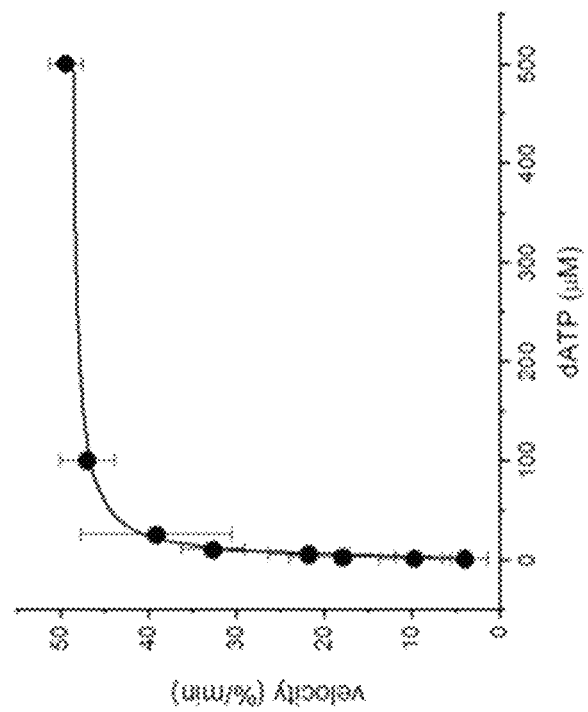
Figure 7B:
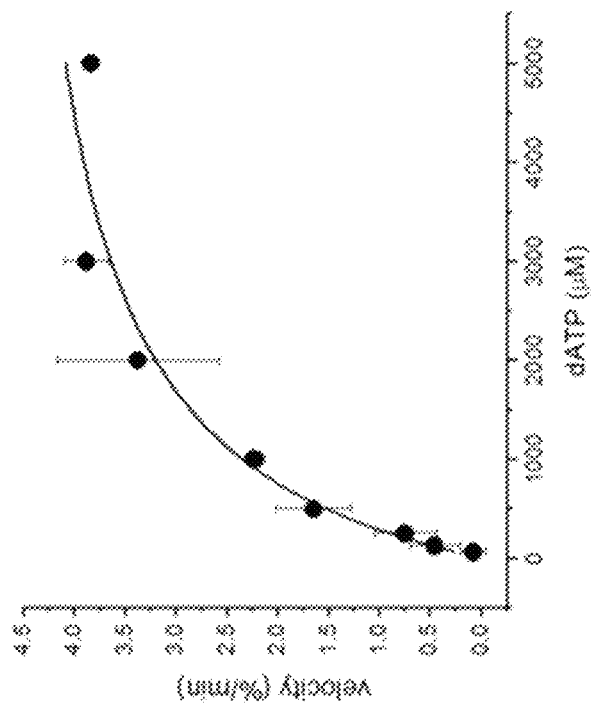
Figure 7C:
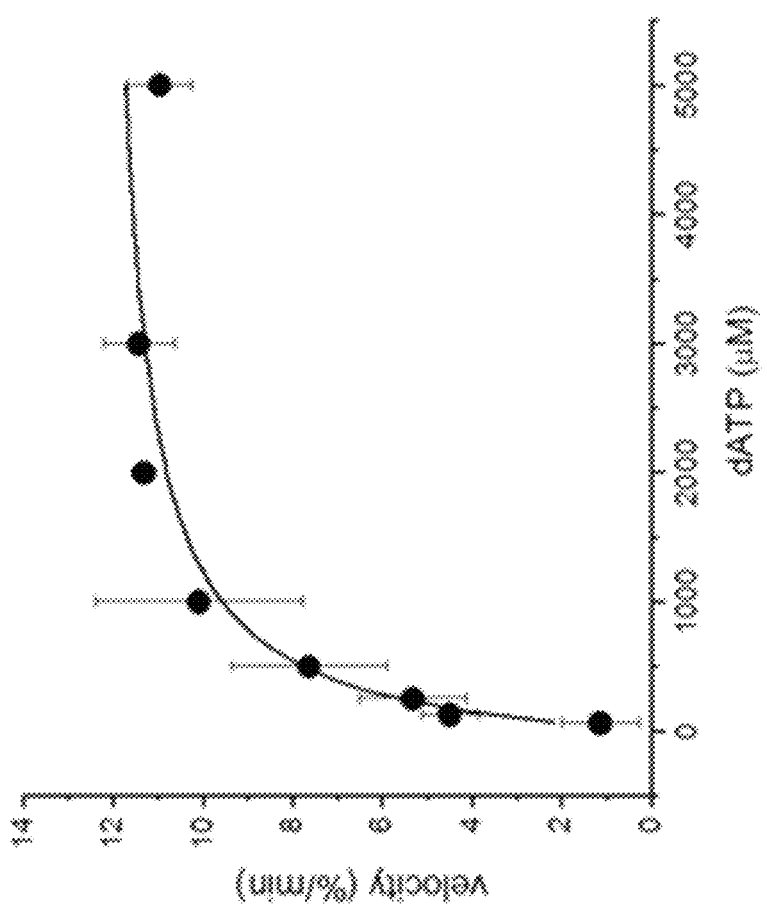
Figures 8A, 8B:
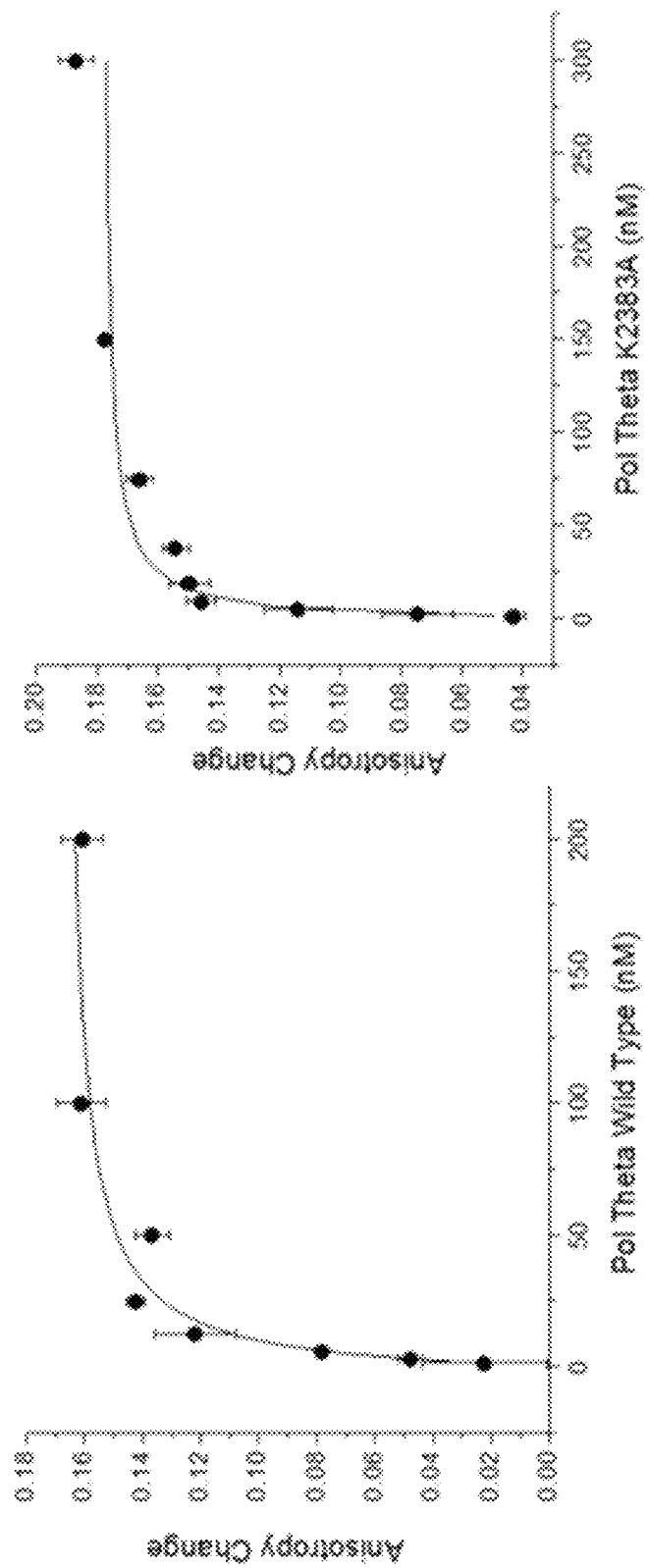
Figure 8D:
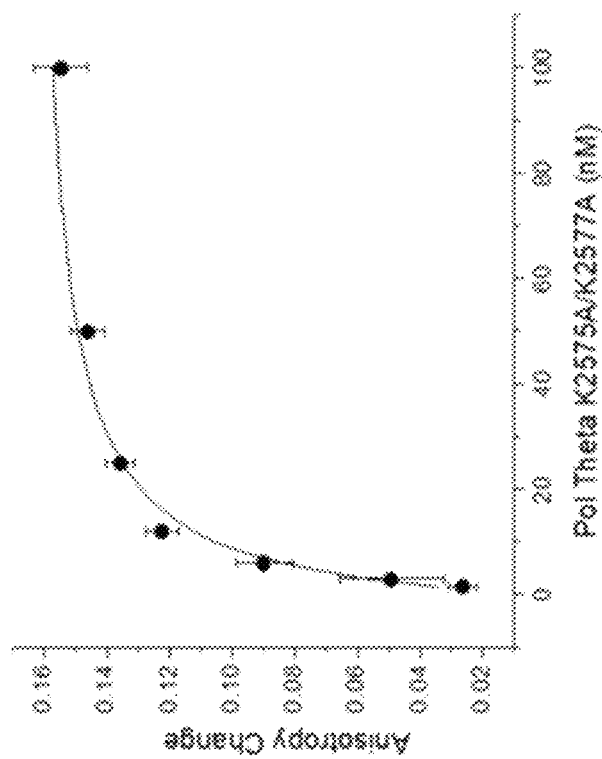
Figure 8C:
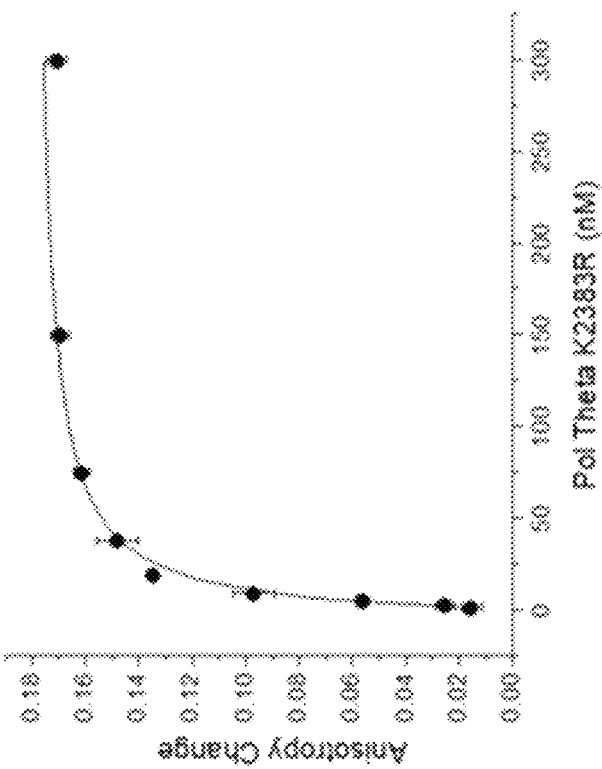
Figure 8E:
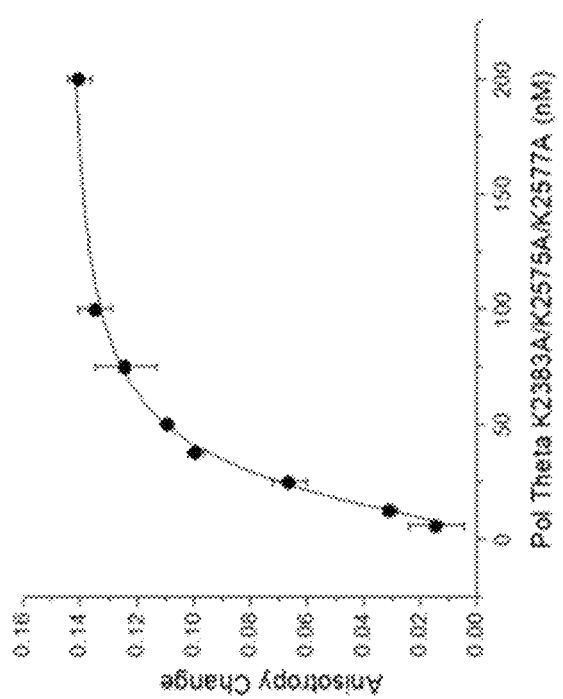
Figures 9A, 9B:
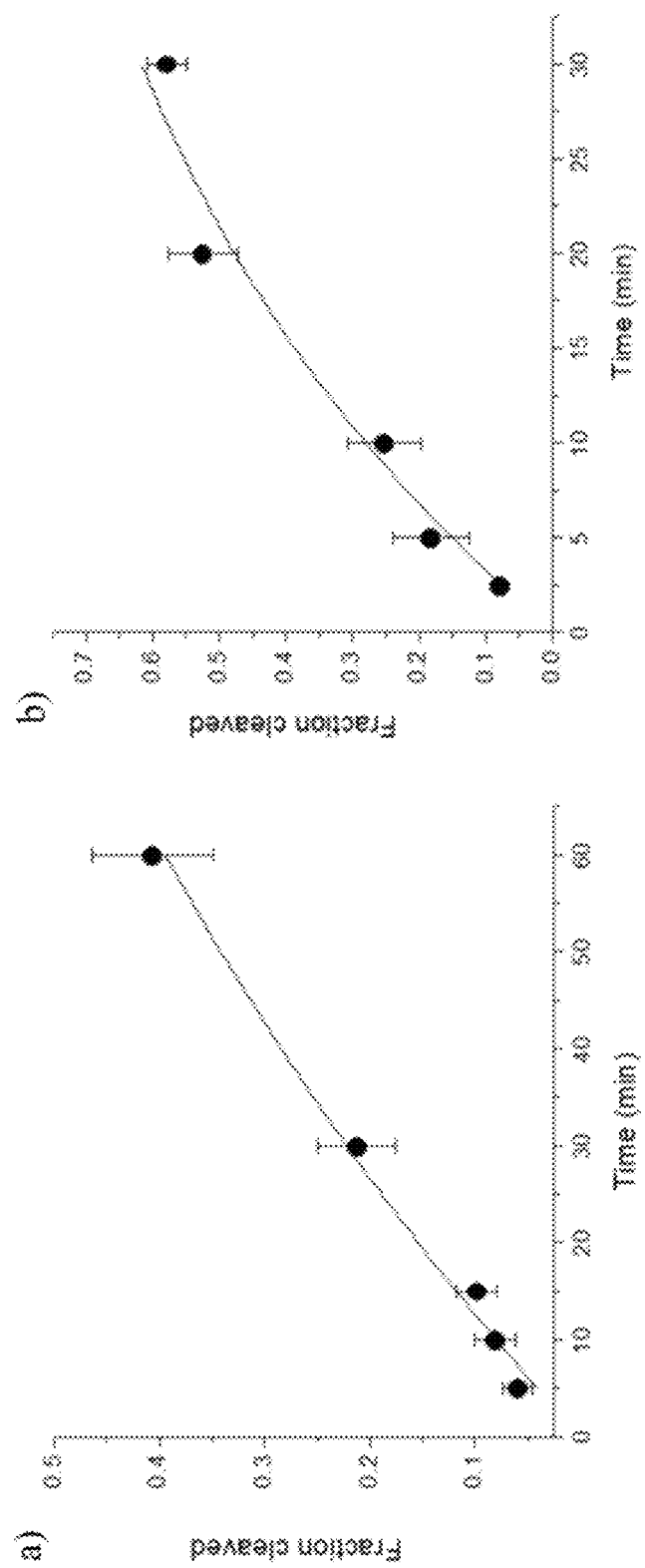
Figure 9D:
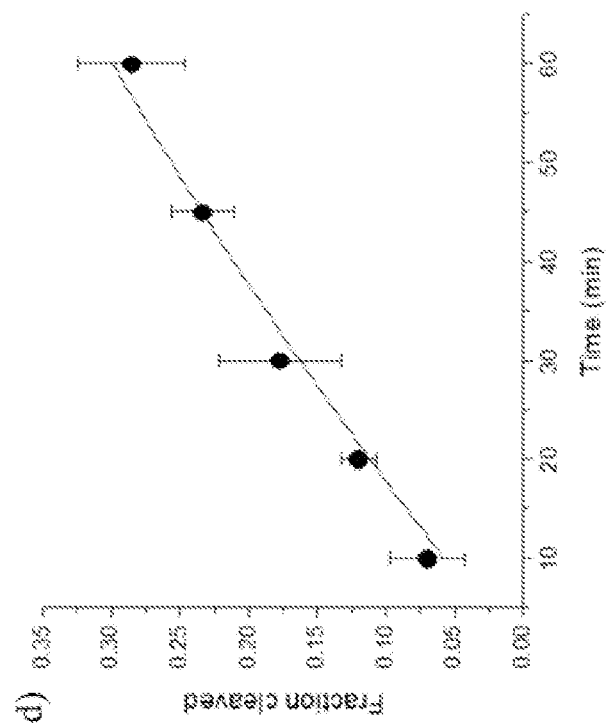
Figure 9C:
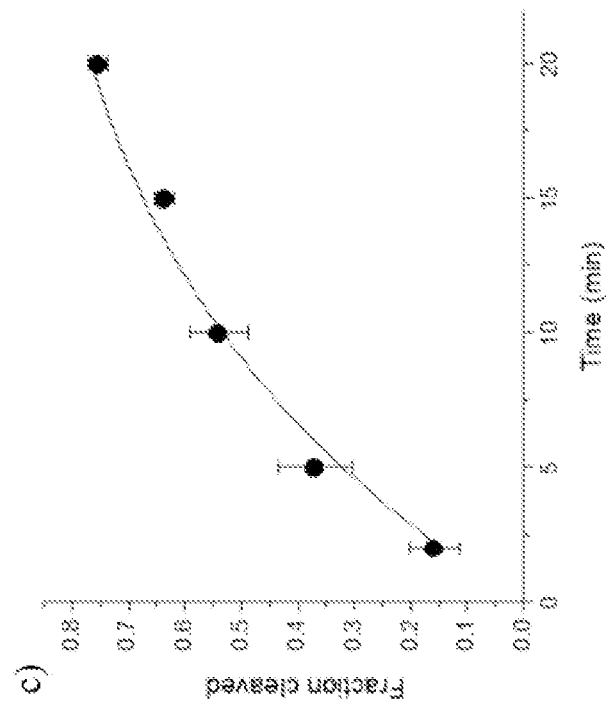
Figure 10:
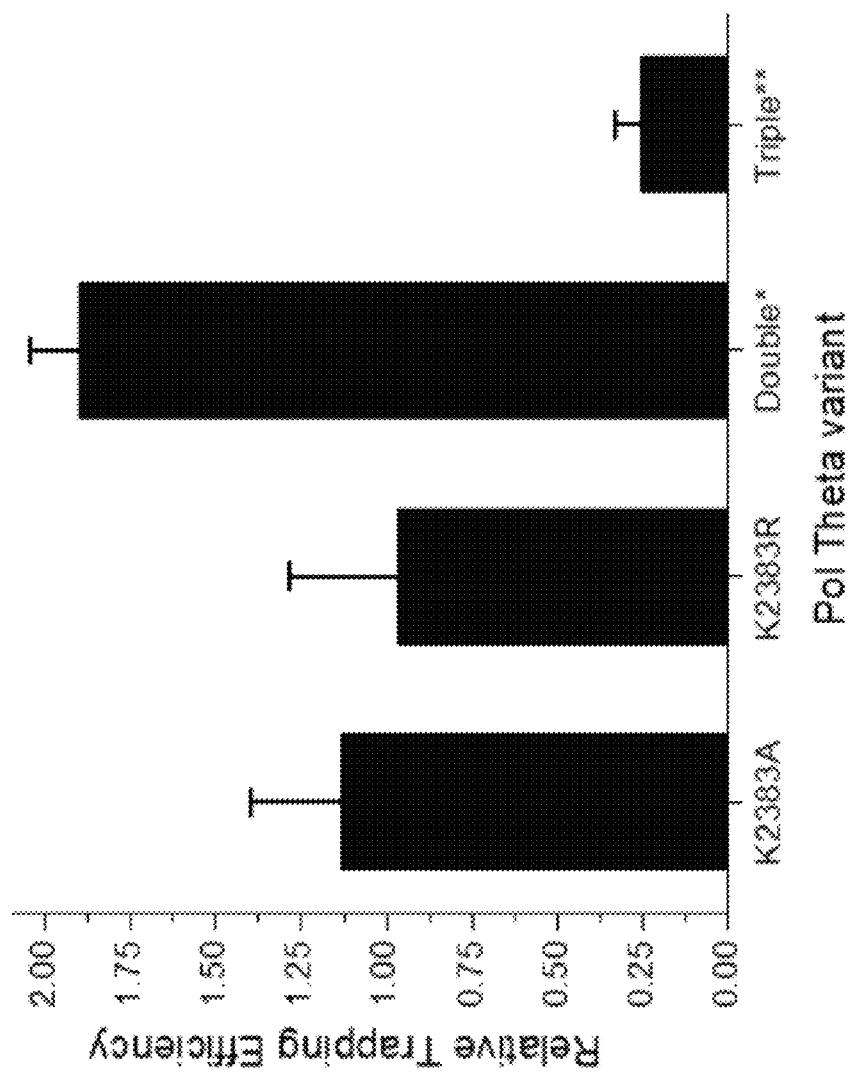

FIG. 6 shows DNA binding ($K_D$) and lyase activity ($k_{Obs}$) of wild type Pol θ and various Lys mutants. *Double=K2575A/K2577A, **Triple=K2383A/K2575A/K2577A. $K_D$ values are the ave.±std. dev. of three experiments utilizing different samples and were determined using 6 via fluorescence anisotropy. The $k_{Obs}$ values are the ave.±std. dev. of at least two experiments determined using 3, each consisting of three replicates;

FIG. 7A, FIG. 7B, and FIG. 7C are sample kinetic plots for dA insertion on 5'-$^{32}$P-5 by Pol θ variants. FIG. 7A is wild type; FIG. 7B is K2383A; and FIG. 7C is K2383R. Data are the average±standard deviation of three replicates;

FIG. 8A, FIG. 8B, FIG. 8C, FIG. 8D, and FIG. 8E are plots for fluorescence anisotropy experiments using Pol θ variants and 6. FIG. 8A is wild type; FIG. 8B is K2383A; FIG. 8C is K2383R; FIG. 8D is K2575A/K2577A; and FIG. 8E is K2383A/K2575A/K2577A. Data are the average±standard deviation of three experiments;

FIG. 9A, FIG. 9B, FIG. 9C, and FIG. 9D are sample kinetic plots for excision of dRP (3'$^{32}$P-1) by Pol θ variants. FIG. 9A is K2383A; FIG. 9B is K2383R; FIG. 9C is K2575A/K2577A; and FIG. 9D is K2383A/K2575A/K2577A. Data are the average±standard deviation of three replicates; and FIG. 10 shows the trapping efficiency (relative to wild type) of Pol θ variants with dRP (3'-$^{32}$P-3) in the presence of NaBH$_4$. *Double mutant=K2575A/K2577A. **Triple mutant=K2383A/K2575A/K2577A. Data are the average±standard deviation of at least three independent experiments.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Identification of DNA Polymerase Theta Inactivation Mechanism

The presently disclosed subject matter provides, in part, the identification of an amino acid in Pol θ that is crucial for its activity. It is believed that this discovery will lead to identification of irreversible inhibitors of Pol θ. More particularly, the presently disclosed subject matter, in part, provides that a particular DNA lesion (pC4-AP), which is produced by a number of agents that oxidatively damage DNA, inactivates Pol θ. Covalent modification of Pol θ allowed the amino acid that is modified to be identified using mass spectrometric analysis of tryptic digests. The amino acid identified, lysine$_{2383}$, is in the polymerase active site. The importance of this amino acid was illustrated by mutating it to alanine and arginine in separate experiments. Both mutations reduced the activity more than 3,000-fold. This insight will allow libraries of molecules to be screened as potential irreversible inhibitors of Pol θ using the approach disclosed in Paul et al., 2017.

As used herein, the term "DNA repair enzyme" includes an enzyme, including Pol θ, that can repair changes or mutations in DNA and restore the DNA to its original state. The presently disclosed methods are applicable for various DNA repair enzymes, including Pol θ, that possess polymerase and/or lyase activity. As used herein, the term "lyase activity" means an activity that involves the removal of a group from a double bond or the addition of a group to a double bond. Accordingly, in some embodiments, the Pol θ inhibitor inhibits the lyase activity of the DNA repair enzyme, e.g., Pol θ. As used herein, the term "polymerase activity" includes the synthesis or assembly of DNA molecules. Non-limiting examples of DNA repair enzymes suitable for use with the presently disclosed methods include DNA polymerase θ. Accordingly, in some embodiments, the Pol θ inhibitor inhibits the polymerase activity of the DNA repair enzyme, e.g., Pol θ.

In some embodiments, the presently disclosed subject matter provides a method for identifying a DNA polymerase theta (Pol θ) inhibitor, the method comprising: (a) contacting Pol θ with one or more candidate Pol θ inhibitors in a Pol θ reaction buffer to form a pre-incubation mixture; (b) incubating the pre-incubation mixture for a period of time at room temperature; (c) diluting the pre-incubation mixture with a solution containing a DNA substrate and nucleotide triphosphates in a Pol θ reaction buffer; and (d) measuring fluorescence of the diluted pre-incubation mixture for a period of time.

In particular embodiments, the presently disclosed subject matter provides a Pol θ inhibitor, or derivative or analog thereof, identified by the presently disclosed screening method.

In other embodiments, the presently disclosed subject matter provides a method for inhibiting Pol θ activity in a subject, the method comprising administering to the subject a therapeutically effective amount of a Pol θ inhibitor, or an analogue or a pharmaceutically acceptable salt thereof. In some embodiments, the inhibiting is irreversible. In other embodiments, the inhibiting is reversible. In particular embodiments, the Pol θ inhibitor inhibits the lyase activity of Pol θ. In yet other embodiments, the Pol θ inhibitor inhibits the polymerase activity of Pol θ. In yet more particular embodiments, the Pol θ inhibitor inhibits the activity of Pol θ by modifying Lys$_{2383}$.

As used herein, the term "inhibit" or "inhibits" has at least two meanings. It may mean to decrease, suppress, attenuate, diminish, arrest, or stabilize the development or progression of a disease, disorder, or condition, the activity of a biological pathway, or a biological activity such as cancer, e.g., by at least 10%, 20%, 30%, 40%, 50%, 60%, 70%, 80%, 90%, 95%, 98%, 99%, or even 100% compared to an untreated control subject, cell, biological pathway, or biological activity. It will be appreciated that, although not precluded, treating a disease, disorder or condition does not require that the disease, disorder, condition or symptoms associated therewith be completely eliminated. The term "inhibit" or "inhibits" may also mean to decrease, suppress, attenuate, diminish, or arrest the activity of an enzyme, which is a biological molecule that accelerates both the rate and specificity of a metabolic reaction. An "inhibitor" is a molecule that inhibits the activity of an enzyme. An "irreversible inhibitor" usually covalently modifies an enzyme and therefore the inhibition cannot be reversed. Irreversible inhibitors may act at, near, or remote from the active site of an enzyme.

In some embodiments, the subject has cancer. A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Proliferation of a cancer cell can include an increase in the number of cells as a result of cell growth and cell division. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas.

Without wishing to be bound to any one particular theory, it is believed that knocking down Pol θ activity can be cytotoxic to a cancer cell. Therefore, in some embodiments, inhibiting Pol θ treats, inhibits, delays, or prevents the spread of the cancer in the subject. In other embodiments, the method further comprises treating, inhibiting, delaying, or preventing the spread of the cancer by inhibiting at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, and changes in the levels of an extracellular protease.

In some embodiments, the presently disclosed subject matter provides a method for inhibiting a cancer cell, the method comprising contacting the cancer or noncancerous cell with a Pol θ inhibitor in an amount effective to irreversibly inhibit Pol θ, thereby inhibiting the cancer cell. By "contacting", it is meant any action that results in a therapeutically effective amount of at least one presently disclosed compound physically contacting at least one cell comprising Pol θ. The method can be practiced in vitro or ex vivo by introducing, and preferably mixing, the compound and cell comprising Pol θ in a controlled environment, such as a culture dish or tube. The method can be practiced in vivo, in which case contacting means exposing at least one cell comprising Pol θ in a subject to a therapeutically effective amount of at least one compound of the presently disclosed subject matter, such as administering the compound to a subject via any suitable route. According to the presently disclosed subject matter, contacting may comprise introducing, exposing, and the like, the compound at a site distant to the cell comprising Pol θ to be contacted, and allowing the bodily functions of the subject, or natural (e.g., diffusion) or man-induced (e.g., swirling) movements of fluids to result in contact of the compound and cell comprising Pol θ. In some embodiments, the method may inhibit Pol θ in vitro, in vivo, or ex vivo.

The presently disclosed methods may further comprise administering to the subject a DNA damaging agent in combination with a Pol θ inhibitor. A "DNA damaging agent" is an agent that damages the DNA structure in some way, such as causing damage in the DNA bases or its sugar phosphate backbone or causing the formation of covalent bonds between the DNA and at least one protein. The DNA damage may affect DNA-histone and DNA-transcription factor interactions and may impact DNA packing, cell division, replication and/or transcription of the DNA.

As provided in more detail herein below, the presently disclosed compounds potentiate the cytotoxicity of a DNA damaging agent whose effects would require repair by Pol θ. In particular embodiments, the DNA damaging agent is administered before, simultaneously, or after administration of the Pol θ inhibitor, or combinations thereof.

A DNA damaging agent may include, for example, γ-radiolysis/ionizing radiation or an agent that produces double strand breaks, including bleomycin, members of the enediyne family of antitumor antibiotics (e.g., esperamicin, calicheamicin, CC107, neocarzinostatin) and related agents.

By "in combination with" is meant the administration of a Pol θ inhibitor, or other compounds disclosed herein, with one or more therapeutic agents, e.g., a DNA damaging agent, either simultaneously, sequentially, or a combination thereof. Therefore, a cell or a subject administered a combination of a Pol θ inhibitor, or other compounds disclosed herein, can receive a Pol θ inhibitor, or other compounds disclosed herein, and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the Pol θ inhibitor, or other compounds disclosed herein, and one or more therapeutic agents are administered simultaneously, they can be administered to the cell or administered to the subject as separate pharmaceutical compositions, each comprising either a Pol θ inhibitor, or other compounds disclosed herein, or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

In particular embodiments, a Pol θ inhibitor and the DNA damaging agent work synergistically to inhibit a cancer cell. As used herein, the terms "synergy," "synergistic," "synergistically" and derivations thereof, such as in a "synergistic effect" or a "synergistic combination" or a "synergistic composition" refer to circumstances under which the biological activity of a combination of a Pol θ inhibitor and another agent, e.g., a DNA damaging agents, including, but not limited to, γ-radiolysis/ionizing radiation or an agent that produces double strand breaks, such as bleomycin or members of the enediyne family of antitumor antibiotics, including esperamicin, calicheamicin, CC107, neocarzinostatin, and related agents, is greater than the sum of the biological activities of the Pol θ inhibitor and the other agent when administered individually.

Synergy, expressed in terms of a "Synergy Index (SI)," generally can be determined by the method described by F. C. Kull, et al., Applied Microbiology 9, 538 (1961), from the ratio determined by:

$$Q_a/Q_A + Q_b/Q_B = \text{Synergy Index(SI)}$$

wherein:

$Q_A$ is the concentration of a component A, acting alone, which produced an end point in relation to component A;

$Q_a$ is the concentration of component A, in a mixture, e.g., a combination of components A and B, which produced an end point in relation to the combination;

$Q_B$ is the concentration of a component B, acting alone, which produced an end point in relation to component B; and $Q_b$ is the concentration of component B, in the mixture, which produced an end point in relation to the combination.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture.

Thus, a "synergistic combination" has an activity higher that what can be expected based on the observed activities of the individual components when used alone. Further, a "synergistically effective amount" of a component refers to the amount of the component necessary to elicit a synergistic effect.

In other embodiments, the presently disclosed subject matter provides a pharmaceutical composition including one Pol θ inhibitor, alone or in combination with one or more additional therapeutic agents in admixture with a pharmaceutically acceptable excipient.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Mechanistic Insight Through Irreversible Inhibition. DNA Polymerase θ Uses a Common Active Site for Polymerase and Lyase Activities

1.1 Abstract

DNA polymerase θ (Pol θ) is a multifunctional enzyme. It is nonessential in normal cells, but its upregulation in cancer cells correlates with cellular resistance to oxidative damage and poor prognosis. Pol θ possesses polymerase activity and poorly characterized lyase activity. The Pol θ lyase activity on various abasic sites was examined and it was determined that the enzyme is inactivated upon attempted removal of the oxidized abasic site commonly associated with C4'-oxidation (pC4-AP). Covalent modification of Pol θ by the DNA lesion enabled determination of the primary nucleophile ($Lys_{2383}$) responsible for Schiff base formation in the lyase reaction. Unlike some other base excision repair polymerases, Pol θ uses a single active site for polymerase and lyase activity. Mutation of $Lys_{2383}$ significantly reduces both enzyme activities, but not DNA binding. Demonstration that $Lys_{2383}$ is required for polymerase and lyase activities indicates that this residue is an Achilles heel for Pol θ and suggests a path forward for designing inhibitors of this attractive anticancer agent.

1.2 Background

Of the seventeen DNA polymerases so far identified in humans, eleven are involved in DNA repair and damage response. See Wu et al., 2017. Five of these repair polymerases, as well as the mitochondrial DNA polymerase (Pol γ), possess lyase activity (Scheme 1A). Lyase activity is frequently associated with excising the remnant (dRP) resulting from abasic site (AP) incision by apurinic endonuclease 1 (Ape1) during base excision repair (BER). See Greenberg, 2014; Matsumoto and Kim, 1995; Garcia-Diaz et al., 2001; Bebenek et al., 2001; Prasad et al., 2009; Prasad et al., 2016; and Longley et al., 1998.

Scheme 1. Base excision repair.

A.

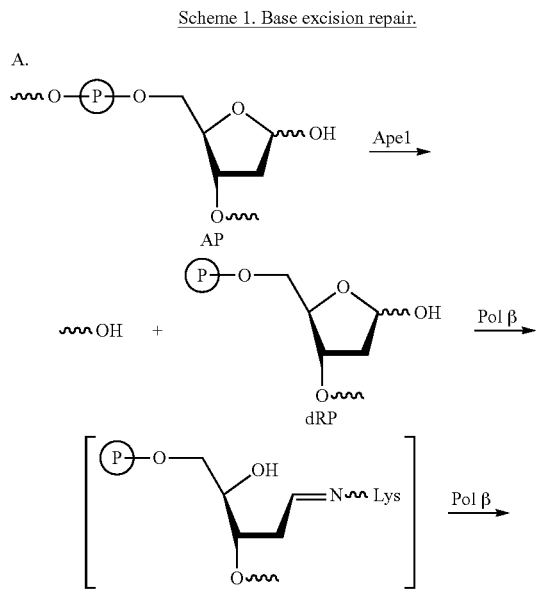

B.

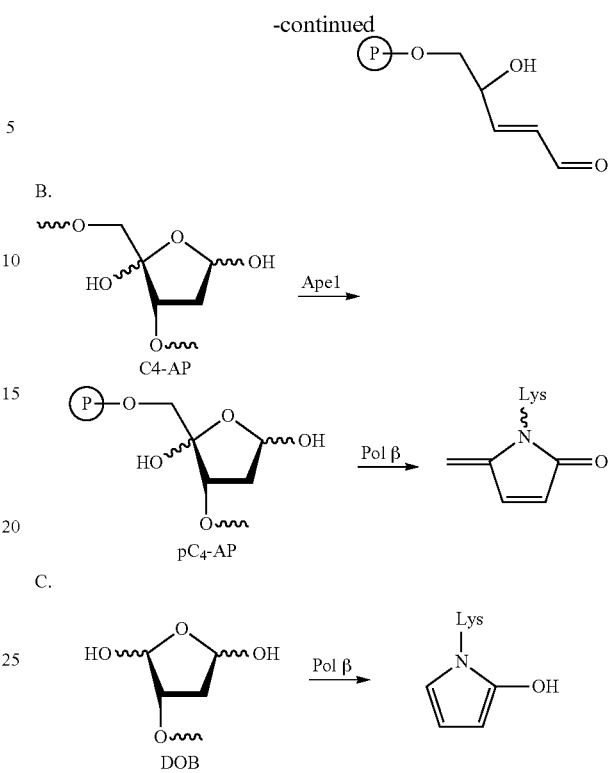

C.

AP and oxidized variants, C4-AP and DOB, are DNA lesions commonly produced as a result of oxidative damage by gradiolysis and chemotherapeutics, including bleomycin. See Dizdaroglu, 2015; Dizdaroglu et al., 2012; Regulus et al., 2007; Burger, 1998; Rabow et al., 1990. pC4-AP produced from C4-AP by Ape1, and DOB, are possible lyase substrates. pC4-AP and DOB, however, irreversibly inhibit DNA polymerase β (Pol β), the primary enzyme responsible for excising dRP (Scheme 1B, C). See Guan and Greenberg, 2010; Jacobs et al., 2011.

The oxidized abasic sites also inactivate DNA polymerase λ (Pol 2), a back-up of Pol β. See Stevens et al., 2013. DNA polymerase θ (Pol θ) promotes resistance to bleomycin and ionizing radiation, suggesting that the interaction of Pol θ with these lesions may be clinically relevant. See Yousefzadeh et al., 2014; Goff et al., 2009. Pol θ is a nonessential enzyme in healthy cells, but homologous recombination-deficient cancers, including many ovarian cancers, are hyper-dependent upon Pol θ expression. See Higgins and Boulton, 2018; Ceccaldi et al., 2015.

Interestingly, Pol θ expression is upregulated in breast, lung, and ovarian cancers, and this correlates with poor prognosis. See Wood and Doublié, 2016. Consequently, Pol θ is an attractive target for synthetic lethal therapy in BRCA-deficient cancers, along with other cancers containing DNA repair defects. Pol θ functions in translesion synthesis and double strand break repair in human cells and also has been implicated in BER. See Yousefzadeh et al., 2014; Yoshimura et al., 2006; Yoon et al., 2014. Like Pol β, Pol θ possesses lyase activity, although little is known about this process. See Prasad et al., 2009.

The presently disclosed subject matter, in part, provides details on Pol θ lyase activity that increases the understanding of this enzymatic process. The presently disclosed subject matter also provides insight into whether Pol θ lyase activity is relevant to the enzyme's ability to enhance cellular resistance to oxidative damage, its validation as an anticancer target, and direction for inhibitor design.

1.3 Results

Figure 1A:
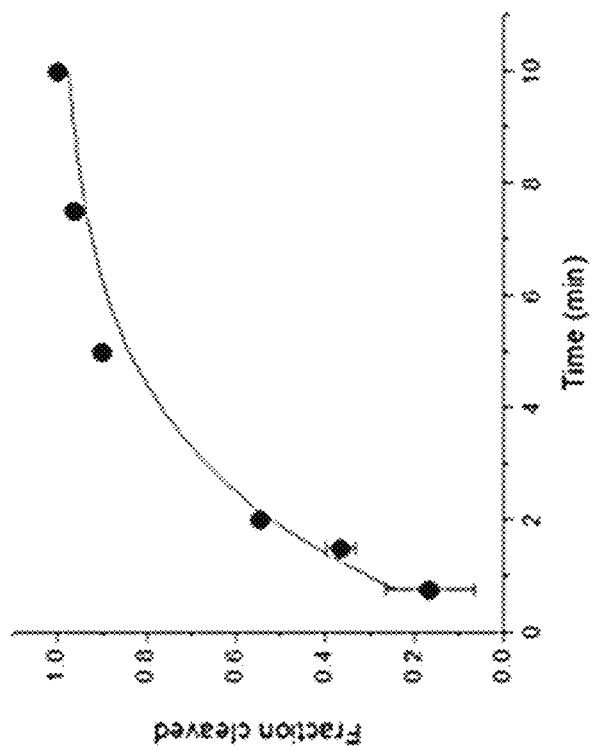
Figure 1B:
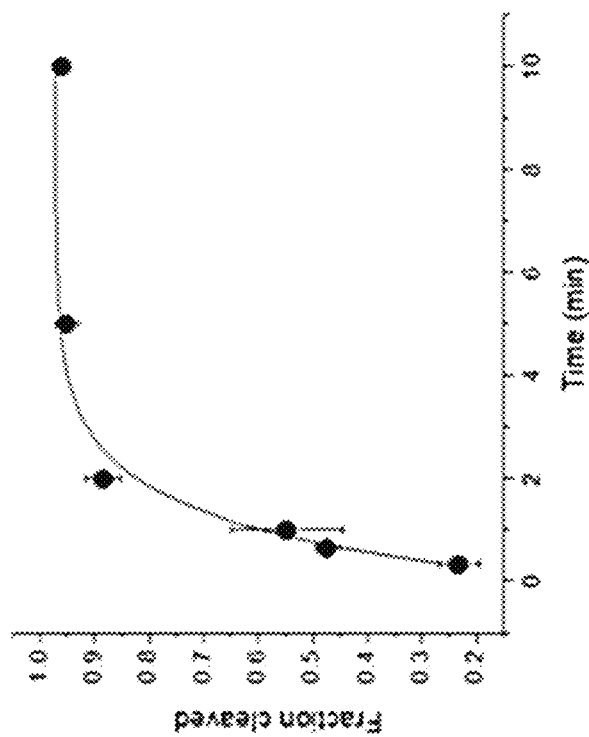
Figure 1C:
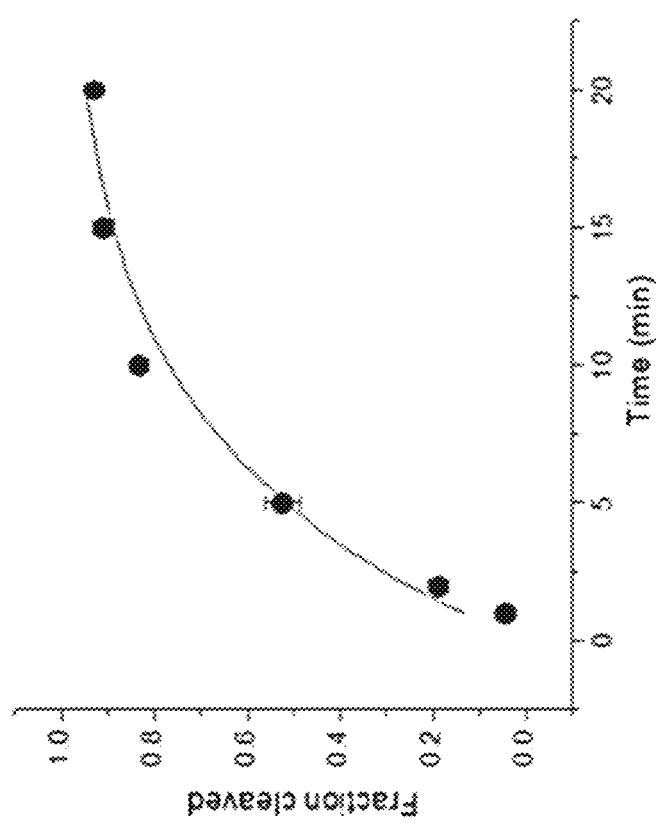

The ability of the 98 kDa Pol θ fragment to excise pC4-AP or DOB was compared to its reactivity with a comparable DNA substrate containing dRP. Under single turnover conditions pC4-AP ($k_{obs}$=0.93±0.11 min$^{-1}$) was excised the most rapidly of the three substrates, but DOB ($k_{obs}$=0.32±0.01 min$^{-1}$) was removed approximately twice as fast as dRP ($k_{obs}$=0.17±0.02 min$^{-1}$) (FIG. 1). The dRP excision rate constant by Pol θ is comparable to a previous report and also is similar to those reported for two other polymerases (Rev1 and Pol ι), but approximately 1,000-fold slower than Pol β. See Prasad et al., 2016; Jacobs et al., 2011; Prasad et al., 2003; and Prasad et al., 2010.

Figures 2A, 2B:
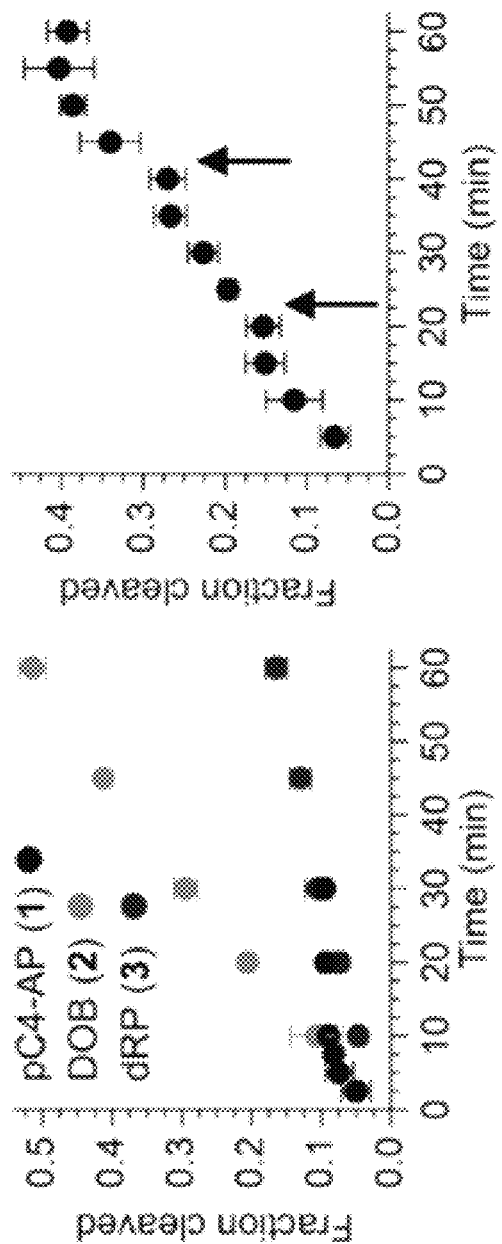

More significantly, under multiple turnover conditions (FIG. 2A), it appeared that pC4-AP excision ceased following 3-4 turnovers. Additional evidence that pC4-AP inactivates Pol θ was obtained by carrying the reaction out under multiple turnover conditions in which additional aliquots of enzyme were periodically added (FIG. 2B). A burst of activity (3-4 turnovers) was observed after the addition of each aliquot, followed by cessation of conversion, consistent with inactivation of Pol θ.

Of the DNA polymerases (Pol β, Pol λ) that are inactivated by oxidized abasic sites (DOB, pC4-AP), Pol θ is the first polymerase that is inactivated by just one. The effect of pC4AP on the enzyme provided an opportunity to identify the source of its lyase activity. The location of Pol θ lyase activity was localized to a 24 kDa region of the polymerase domain, but the specific lysine responsible for Schiff base formation was unknown. See Prasad et al., 2016.

Scheme 2. Modification of Pol θ

```
              SEQ ID NO: 2
5'-d(TAA TGG CTA ACG CTT   XCC GTA ATG CAG TCT)
3'-d(ATT ACC GAT TGC GAA   AGG CAT TAC GTC AGA)
              SEQ ID NO: 3
                        1 X = pC4-AP
                        2 X = DOB
                                    SEQ ID NO: 4
5'-d(TAA TGG CTA ACG CAA   XAC GTA ATG CAG TCT)
3'-d(ATT ACC GAT TGC GTT   ATG CAT TAC GTC AGA)

3 X = dRP
```

Figures 3A, 3B:
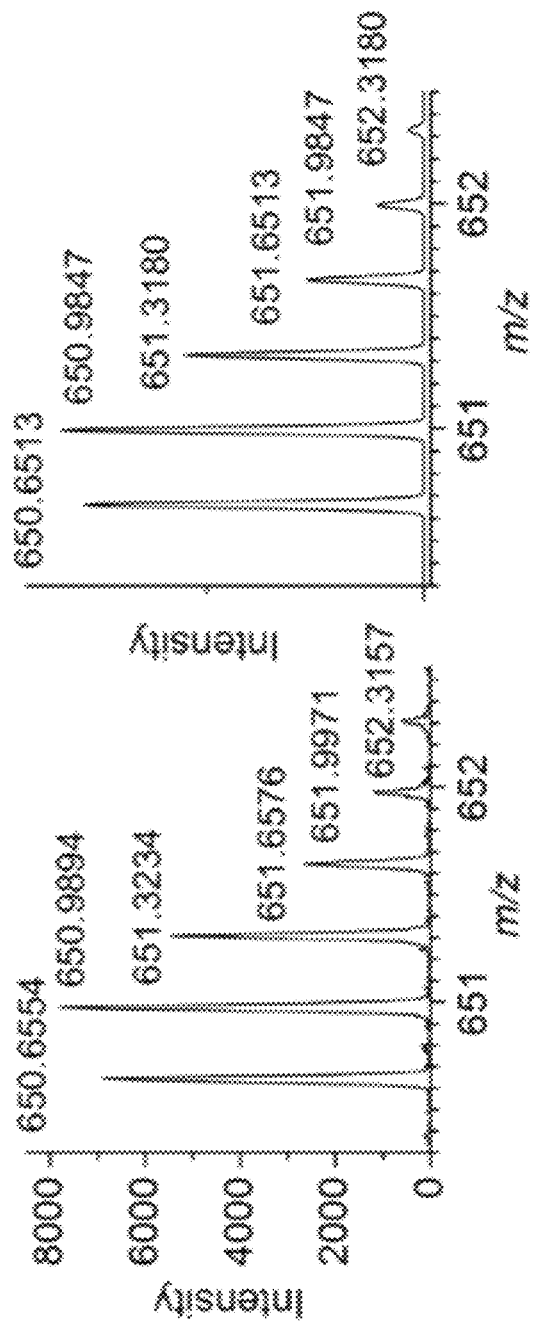

Pol θ was subjected to trypsin digestion following incubation with excess 1 (see Scheme 2). A single modified peptide (FIG. 3A), whose mass (z=3) corresponded to 4 (FIG. 3B), was identified by LC-MS/MS.

SEQ ID NO: 1

4

H$_2$N—Q$_{2380}$QA K$_{2383}$QI CYG IIY GMG AK$_{2396}$

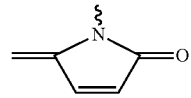

Figure 4:
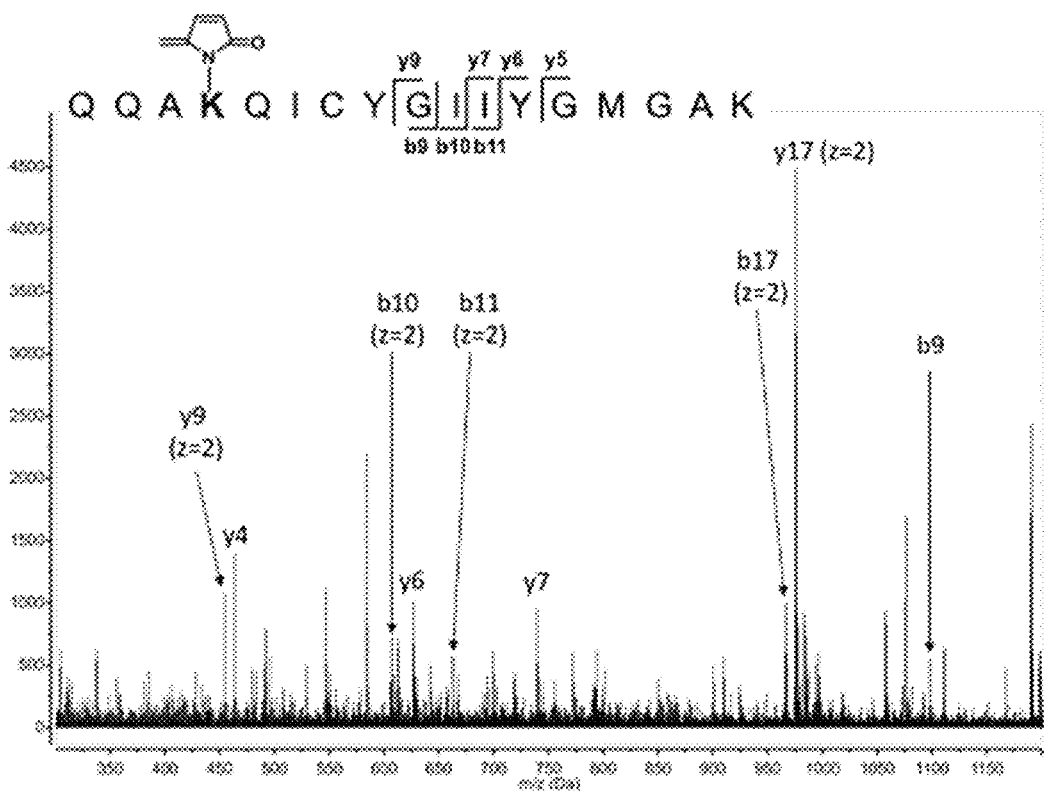
FIG. 4 is the annotated MS/MS spectrum of modified peptide 4 (SEQ ID NO: 1)

The peptide encompasses amino acids 2380-2396 in Pol θ (observed mass=1948.9606 Da, calculated mass=1948.9540 Da), and contains two tyrosine residues in addition to a more nucleophilic, internal lysine (Lys$_{2383}$). Fragmentation of 4 (FIG. 4) is consistent with Lys$_{2383}$ modification.

Figure 5:
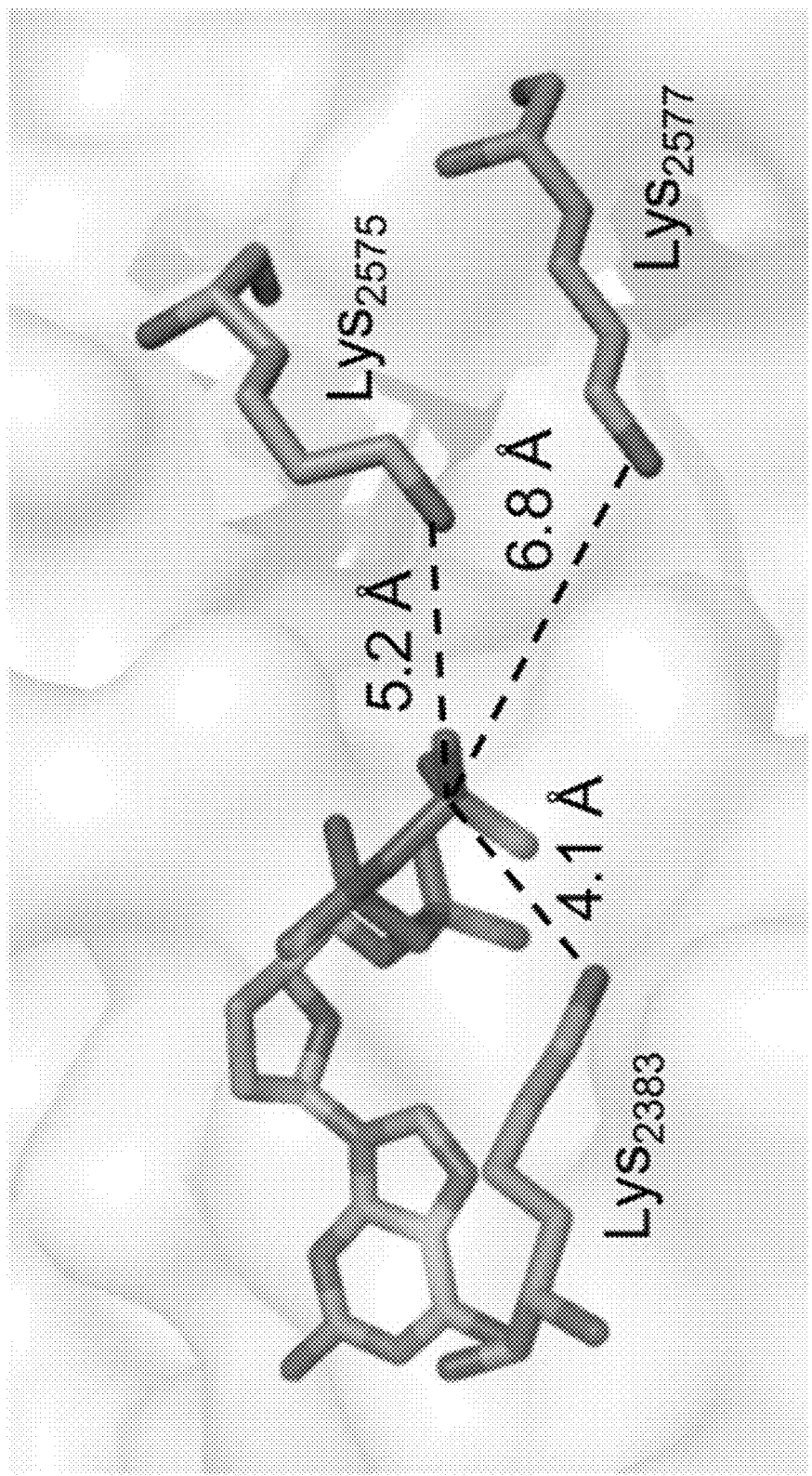
FIG. 5 is the Pol θ structure showing $Lys_{2383}$ and other potential nitrogen nucleophiles. (PDB: 4X0Q)

The X-ray co-crystal structure of Pol θ with DNA and ddGTP reveals that Lys$_{2383}$ complexes the incoming nucleotide triphosphate within the polymerase active site (FIG. 5). See Zahn et al., 2015. Formation of 4 suggests that, unlike Pol β and Pol λ, Pol θ uses a single active site to carry out polymerase and lyase reactions. See Garcia-Diaz et al., 2001; Prasad et al, 1998.

Scheme 3. Mutation of Lys$_{2383}$ to alanine (K2383A) and arginine (K2383R).

```
SEQ ID NO: 6  5'-d(AGC TGC AGG TCC TA)
SEQ ID NO: 7  3'-d(TCG ACG TCC AGG ATT TAC GTA CAC TCC GGA)

5

SEQ ID NO: 2  5'-d(TAA TGG CTA ACG CTT   XCC GTA ATG CAG TCT)
SEQ ID NO: 7  3'-d(ATT ACC GAT TGC GAA   AGG CAT TAC GTC AGA)
```

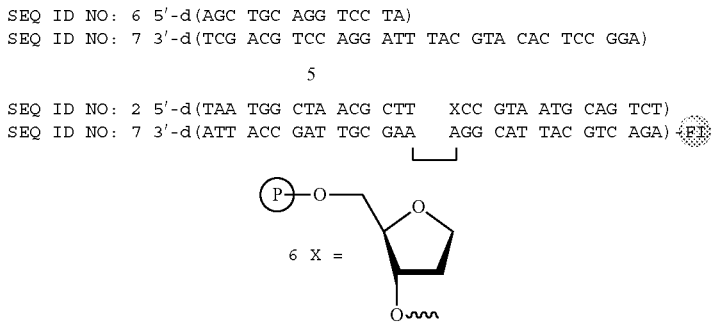

6 X =

The function of Lys$_{2383}$ was investigated further by mutating it to alanine (K2383A) and arginine (K2383R) (Scheme 3; Table 1). The $K_m$ for dA incorporation in 5 by K2383A is more than 50-times higher than wild type Pol θ and $k_{cat}$ is reduced >100-fold. The polymerase activity ($k_{cat}/K_m$) of K2383R, which retains positive charge for possible dNTP binding, is approximately 10-fold greater than the alanine mutant, but is still more than 3,000-times less active than wild type enzyme (FIG. 7). DNA binding, however, as measured via fluorescence anisotropy on 6 (FIG. 6, FIG. 8), is unaffected by either mutation.

TABLE 1

Polymerase activity of wild type Pol θ and mutants.[a]

| Pol θ variant | $K_m$ (µM)[b] | $k_{cat}$ (min$^{-1}$)[b] | $k_{cat}/K_m$ (µM · min)$^{-1}$ |
|---|---|---|---|
| wt28 | 5 ± 1 | 65 ± 12 | 13.6 |
| K2383A | 1094 ± 37 | 0.5 ± 0.1 | 4.8 × 10−4 |
| K2383R | 311 ± 24 | 1.4 ± 0.2 | 4.3 × 10−3 |

[a]Kinetics of dA incorporation in 5 were measured.
[b]Data are the ave. ± std. dev. of two experiments each consisting of three replicates.

The K2383A and K2383R mutants also exhibit significantly decreased lyase activity on dRP (FIG. 6, FIG. 9). dRP excision is reduced by 90% when $Lys_{2383}$ is replaced by alanine, whereas K2383R retains approximately 20% of the wild type enzyme's lyase activity. A previous study showed that the polymerase and lyase activities of Pol θ reside in a common domain. See Prasad et al., 2009. Mutation of Asp2540 and Glu2541 eliminated polymerase activity, but not lyase activity, suggesting that the two are independent of one another. See Prasad et al., 2009. Mutation of $Lys_{2383}$ to alanine (K2383A) or arginine (K2383R) reveals that the two activities share a common residue.

Based on the observation of residual lyase activity in the K2383A and K2383R mutants, whether other lysine residues were involved in the lyase reaction was considered. DNA-protein cross-links (DPCs) were detected when mixtures of K2383A or K2383R and 3 were incubated in the presence of $NaBH_4$ (FIG. 10). The observation of DPCs in experiments with mutant proteins could indicate that an additional nucleophile(s) was present in the enzyme, or that $Lys_{2383}$ may not even be the primary nucleophile responsible for Schiff base formation. For instance, Pol β utilizes a backup residue, proposed to be Lyssa, for this function when the primary nucleophile, $Lys_{72}$ is removed. See Prasad et al., 1998; Prasad et al., 2005. Alternatively, precedent also exists for the $NaBH_4$ experiments providing misleading information regarding nucleophilic lysine residues in repair enzymes. See Williams and David, 1999.

To further investigate the proposed function of $Lys_{2383}$ as the major nucleophile, additional Pol θ mutants were prepared. A crystal structure for Pol θ bound to a BER substrate is unavailable, so the crystal structure of Pol θ in a ternary complex with a primer-template and incoming ddGTP (PDB: 4X0Q) was utilized to identify potential alternative nucleophiles. See Zahn et al., 2015. Using the phosphate coordinated to $Lys_{2383}$ as a point of reference, it was determined that $Lys_{2575}$ and $Lys_{2577}$ were the only nucleophilic residues within the active site within 10 Å. Mutation of these two residues in addition to $Lys_{2383}$ (K2383A/K2575A/K2577A) reduced lyase activity to 3% of the wild type and reduced Schiff base trapping by 80% (FIG. 6, FIG. 7). This suggests that $Lys_{2575}$ and $Lys_{2577}$ may compensate for lyase activity in the absence of $Lys_{2383}$; however, binding of 6 by the triple mutant was approximately four-fold weaker than wild type Pol θ, indicating that other factors may contribute to this observation. Despite the possible role for $Lys_{2575}$ or $Lys_{2577}$ in lyase activity, neither residue is the primary nucleophile as the double mutant (K2575A/K2577A) showed only 50% reduction in lyase activity while binding 6 as strongly as wild type Pol θ (FIG. 6). Interestingly, Schiff base trapping was increased more than two-fold for the K2575A/K2577A mutant (FIG. 10), suggesting a possible role for one or both of these residues in a step following Schiff base formation, perhaps in deprotonation of the CT-position.

Several polymerases also possess the ability to excise dRP via Schiff base formation and may participate in BER. The X-family polymerases Pol β and Pol λ contain an 8-kDa lyase domain, separate from the polymerase domain, where dRP excision is conducted. See Garcia-Diaz et al., 2001; Prasad et al., 1998; and Belousova et al., 2015. Four additional polymerases, Pol θ, Pol ι, Rev1, and the mitochondrial polymerase Pol γ, possess lyase activity, yet they lack a similar 8-kDa lyase domain. See Prasad et al., 2009; Prasad et al., 2016; Longley et al., 1998; and Prasad et al., 2003.

Unlike Pol β and Pol λ, the major catalytic nucleophile is unknown for each of these polymerases. Inactivation of Pol θ by pC4-AP served two purposes. Firstly, it suggests that Pol θ induced cellular resistance to bleomycin is not due to the enzyme assisting in excision of C4-AP in addition to its established role in double-strand break repair. See Yousefzadeh et al., 2014. Moreover, inactivation of the enzyme enabled it to be determined that $Lys_{2383}$ is the major nucleophile for Pol θ lyase activity. Importantly, this residue also is essential for efficient polymerase activity, consistent with the crystal structure of Pol θ, where $Lys_{2383}$ coordinates the γ-phosphate of the incoming dNTP. See Zahn et al., 2015. This is the first demonstration that a single residue functions in both lyase and polymerase activities for any BER polymerase. A previous study on Pol ι showed that mutation of a single residue, $Lys_{207}$, reduced both polymerase and lyase activity. See Miropolskaya et al., 2017. This residue, however, was proposed to be important for DNA binding (see Miropolskaya et al., 2017) as opposed to a direct role in lyase and polymerase activities, as demonstrated for $Lys_{2383}$ of Pol θ. Oligonucleotide substrates containing lesions (e.g., DOB, pC4-AP) capable of inactivating the lyases may be generally useful tools for identifying the key nucleophilic residues in such enzymes.

Identification of $Lys_{2383}$ as the residue responsible for Schiff base formation may have ramifications beyond its fundamental biochemical significance. DNA repair enzymes are active anticancer targets. See Tahara et al., 2018; Zafar and Eoff, 2017; Gowda et al., 2017; Paul et al., 2017; Donley et al., 2015; and Zafar et al., 2018. Pol θ is especially interesting in this regard because it is nonessential for healthy cells, but provides therapeutic resistance in cancer cells. The potential of Pol θ as an anticancer target was recently compared to poly(ADP-ribose) polymerase, a target that has attracted a great amount of attention, resulting in clinically successful inhibitors. See Higgins and Boulton, 2018; Muvarak et al., 2016; and Murai et al., 2012. Determination that modification of $Lys_{2383}$ inactivates Pol θ represents an Achilles heel of this enzyme, the modification of which eviscerates its polymerase and lyase functions. The identification of a single nucleophilic residue within the active site of Pol θ suggests that a previously reported approach used for identifying Pol inhibitors will be useful against this enzyme. See Paul et al., 2017.

1.4 Experimental Methods 1.4.1. General Methods Oligonucleotides were synthesized on an Applied Biosystems Inc. 394 DNA synthesizer using reagents from Glen Research (Sterling, Va.) and deprotected according to the manufacturer's instructions. γ-$^{32}$P-dATP and α-$^{32}$P-ATP (cordycepin) were obtained from PerkinElmer. Protein purification was conducted using an AKTA FPLC and columns were from GE Healthcare. $C_{18}$ Sep Pak cartridges were from Millipore. T4 polynucleotide kinase, terminal deoxynucleotidyl transferase, Dpn1, Phusion polymerase, and dNTPs were obtained from New England Biolabs. Sephadex G-25 was from GE Healthcare. DH5a E. coli were from Invitrogen. Trypsin/Lys-C mix was from Promega. Analysis of radiolabeled oligonucleotides was carried out using a Storm 860 Phosphorimager and ImageQuant 7.0 TL software. LC-MS/MS analysis was conducted using Waters Acquity/Xevo-G2 UPLC-MS system. ESI-MS was conducted using a Thermoquest LCQ Deca. MALDI-TOF MS was conducted using a Bruker Autoflex III MALDI TOF. Sanger sequencing was conducted by the Genetic Resources Core Facility at Johns Hopkins. Fluorescence anisotropy measurements were conducted using an AVIV Biomedical Model ATF 107 spectrofluorometer at the Center for Molecular Biophysics at Johns Hopkins University. Photolyses were carried out in a Rayonet photoreactor fitted with 16 lamps having a maximum output at 350 nm.

Pol θ catalytic core (residues 1792-2590) was expressed and purified as previously described. Hogg et al., 2011; Malaby et al., 2017. Polymerase active site titration of wild type Pol θ was reported previously. Laverty et al., 2017. All oligonucleotides were purified by 20% denaturing polyacrylamide gel electrophoresis (PAGE) and desalted by C18 Sep Pak. Modified oligonucleotides were characterized by ESI-MS or MALDI-MS. Phosphoramidites of photochemical precursors to pC4-AP, DOB, and 5'-dRP were synthesized as previously described and incorporated into oligonucleotides by solid-phase synthesis. Guan and Greenberg, 2010; Kim et al., 2003; and Sczepanski et al., 2010.

1.4.2 Preparation of Oligonucleotide Complexes. For lyase experiments, oligonucleotides containing the appropriate photochemical precursor were 3'-$^{32}$P-labeled. The oligonucleotide (100 pmol) was incubated (37° C., 2 h) with α-$^{32}$P-ATP (30 µCi) and terminal transferase (40 units) in a 50 µL reaction in the terminal transferase and $CoCl_2$ buffers provided by the manufacturer. For primer extension experiments, the primer strand was 5'-$^{32}$P-labeled. The primer (100 pmol) was incubated (37° C., 1.5 h) with γ-$^{32}$P-ATP (20 µCi) and T4 polynucleotide kinase in the reaction buffer provided by the enzyme manufacturer. Following incubation, unincorporated radionuclides were removed by Sephadex G-25 spin column. Ternary complexes 1-3 were prepared by mixing 3'-$^{32}$P-labeled oligonucleotide with the appropriate template and flanking strand in a 1:1.5:3 ratio in phosphate buffered saline (10 mM sodium phosphate, 100 mM NaCl, pH 7.2), heating to 95° C., and slowly cooling to 25° C. Primer-template complex 5 was prepared in the same fashion, but the 5'-$^{32}$P-labeled primer strand and the template were mixed in a 1:1.5 ratio. Ternary complex 6 used for fluorescence anisotropy measurements was prepared by annealing the fluorophore-labeled template with the other two strands in a 1:1.5:1.5 ratio. For lyase experiments, pC4-AP, DOB, and 5'-dRP were generated immediately before the start of the experiment by photolysis (350 nm, 10 min) of the ternary complex containing the appropriate photochemical precursor. For every experiment, complete photolysis was confirmed by treatment with NaOH (0.1 M, 15 min, 37° C.), which gave quantitative cleavage of 5'-dRP, DOB, and pC4-AP.

1.4.3. Steady-state kinetic analysis of dA incorporation in 5 by Pol θ. Polymerase reactions were conducted with Pol θ (432 pM for wild type Pol θ and 5 nM for K2383A and K2383R), 5'-$^{32}$P-5 (50 nM), and a range of dATP concentrations (0.25 µM-100 µM for wild type and 62.5-5000 µM for mutants) at 25° C. in reaction buffer (10 mM Tris HCl pH 8, 25 mM KCl, 10 mM $MgCl_2$, 1 mM BME). The concentration range for dATP and the reaction time were selected so that reactions proceeded no further than 25% (single-hit conditions). In a typical experiment, a 2×DNApolymerase solution was prepared by mixing 5'-$^{32}$P-5 (500 nM, 18 µL), 10×reaction buffer (18 µL), 10×Pol θ (4.32 nM for wild type or 50 nM for mutants, 18 µL) in storage buffer (20 mM Tris HCl pH 7, 300 mM NaCl, 10% glycerol, 5 mM BME), and $H_2O$ (36 µL). The 2×DNAenzyme solution (3 µL) was mixed with the appropriate 2×dNTP solution (3 µL) to initiate the reaction. Reactions were incubated for 20 s for wild type Pol θ, 1.5 min for K2383R, and 4 min for K2383A, after which, they were quenched with 95% formamide loading buffer containing 25 mM EDTA (6 µL). An aliquot (4 µL) was analyzed by 20% denaturing PAGE run at 55 W for approximately 3.5 h. The gel was analyzed by phosphorimaging, and the data were fit to the Michaelis-Menten equation. The $k_{cat}$ was determined by dividing $V_{max}$ by the active concentration of enzyme. Active site titrations could not be carried out on mutant proteins due to extremely slow reaction rates. Hence, the active fraction was assumed to be equal for mutant and wild type proteins.

1.4.4. Analysis of Pol θ lyase activity under multiple turnover conditions. Ternary complexes 3'-$^{32}$P 1-3 (100 nM) were incubated with Pol θ (2.5 nM) at 37° C. in a reaction buffer consisting of 50 mM HEPES pH 7.5, 20 mM KCl, 1 mM EDTA, 1 mM β-mercaptoethanol. In a typical experiment, a 10× solution of DNA (500 nM) in 1× phosphate buffered saline (10 mM sodium phosphate 100 mM NaCl, pH 7.2) was prepared and photolyzed (350 nm, 10 min) to generate the appropriate abasic site (dRP, DOB, or pC4-AP). The 10×DNA solution (3 µL) was added to a solution of $H_2O$ (21 µL) and 10× reaction buffer (3 µL). A 10× solution of Pol θ (3 µL) in storage buffer (20 mM Tris HCl pH 7, 300 mM NaCl, 10% glycerol, 5 mM BME) was added and the reaction was incubated at 37° C. To account for the background reaction in the absence of enzyme, a control sample was treated in the exact same fashion except instead of adding Pol θ to the reaction, the same volume of Pol θ storage buffer (3 µL) was added. Aliquots were removed from the reaction and frozen on dry ice at 2.5, 5, 7.5, 10, 20, and 30 min for 1 and 10, 20, 30, 45, and 60 min for 2 and 3. At the end of the experiment, a 500-mM solution of $NaBH_4$ was prepared in $H_2O$ and immediately added (1 µL) to each aliquot to quench the reaction. The reduction of the substrate was nearly instantaneous, but residual $NaBH_4$ sometimes interfered with mobility during gel electrophoresis, so the reactions were incubated at room temperature for 1.5 h with occasional centrifugation on a bench-top centrifuge to allow for complete reaction of residual $NaBH_4$. Alternatively, ethanol precipitation could be used to remove excess $NaBH_4$ without the necessity of a prolonged incubation, but this was typically not employed. Following quenching of the reactions, samples were mixed with an equal volume (5 µL) of 95% formamide containing 10 mM EDTA and trace bromophenol blue and xylene cyanol and subjected to 20% denaturing polyacrylamide gel electrophoresis at 55 W for approximately 4 h. The gel was exposed to a phosphor storage cassette and imaged using phosphorimaging. The fraction of product formed in the background reaction without enzyme was subtracted from each time point, and the resulting fraction of product formed by enzymatic reaction was plotted as a function of time. Reactions were conducted in triplicate for each experiment and each experiment was conducted at least twice.

1.4.5. Comparison of single turnover lyase kinetics for dRP excision by Pol θ variants. Ternary complex 3'-$^{32}$P-3 (50 nM) were incubated with a large excess (1 µM) of Pol θ (wild type, K2383A, K2383R, K2575A/K2577A, or K2383A/K2575A/K2577A) at 37° C. in reaction buffer consisting of 50 mM HEPES pH 7.5, 20 mM KCl, 1 mM EDTA, 1 mM β-mercaptoethanol. Aliquots (4 µL) were removed and frozen on dry ice at 1, 2, 5, 10, 15, 20 min for the wild type; 2, 5, 10, 20, and 30 min for K2383R mutant; 2, 5, 10, 15, and 20 min for K2575A/K2577A and 5, 10, 15, 30, and 60 min for K2383A and K2383A/K2575A/K2577A. The experimental procedure was the same as for multiple turnover conditions, including accounting for noncatalyzed reaction, except for the noted differences in concentration and reaction times. The fraction of product was plotted as a function of reaction time and the data were fit to the equation fraction cleaved=(maximum fraction cleaved) $(1-e^{k_{obs}*time})$.

Reactions were conducted in triplicate for each experiment and each experiment was conducted at least twice.

1.4.6. Comparison of single turnover lyase kinetics for dRP, DOB, and pC4-AP excision by wild type Pol θ. Experimental conditions were the same as the previous section except aliquots were removed at 20 s, 40 s, 1 min, 2 min, 5 min, and 10 min for pC4-AP (3'-$^{32}$P-1); 45 s, 90 s, 2 min, 5 min, 7.5 min, and 10 min for DOB (3'-$^{32}$P-2); and 1, 2, 5, 10, 15, and 20 min for dRP (3'-$^{32}$P-3).

1.4.7. Inhibition of Pol θ Lyase Activity by pC4-AP. Pol θ (5 nM) was incubated with pC4-AP (3'-$^{32}$P- 1, 100 nM) in reaction buffer (50 mM HEPES pH 7.5, 20 mM KCl, 2 mM DTT, 1 mM EDTA) at 25° C. A 10×solution of 3'-32P- 1 was prepared by photolysis (10 min, 350 nm) and 7 μL of this solution was added to a microcentrifuge tube containing H$_2$O (49 μL) and 10× reaction buffer (7 μL). The reaction was initiated by the addition of a 10× solution of Pol θ (7 μL, 350 fmol) in storage buffer (20 mM Tris·HCl pH 7, 300 mM NaCl, 10% glycerol, 5 mM BME) bringing the volume of the reaction to 70 μL. To account for the background reaction in the absence of enzyme, a control sample was treated in the exact same fashion except instead of adding Pol θ to the reaction, the same volume of Pol θ storage buffer was added. Aliquots (4 μL) were removed from the reactions at 5, 10, 15, and 20 min and frozen on dry ice. Immediately after removing the aliquot at 20 min, an aliquot (350 fmol, 1 μL) of Pol θ in storage buffer was added to the reaction. Aliquots were removed at 25, 30, 35, and 40 min and frozen on dry ice. Another aliquot of Pol θ in storage buffer (350 fmol, 1 μL) was added immediately after removing the aliquot at 40 min. Aliquots were removed from the reaction at 45, 50, 55, and 60 min and frozen on dry ice. Reactions were quenched with NaBH$_4$ (1 μL, 500 mM) and analyzed by polyacrylamide gel electrophoresis and phosphorimaging. The fraction of product formed in the background reaction without enzyme was subtracted from each time point, and the resulting fraction of product formed by enzymatic reaction was plotted as a function of time. Reactions were conducted in triplicate for each experiment and each experiment was conducted at least twice.

1.4.8. Generation of Pol θ mutants. Pol θ variants were generated by site-directed mutagenesis of the Pol θ plasmid reported previously. Hogg et al., 2011. PCR was conducted with the following primers: primers for the K2383A mutation were 5'-d(CTG AGG CAG GCA CAG ATT TGC TAT GGG ATC A) (SEQ ID NO: 8) and 5'-d(TGA TCC CAT AGC AAA TCT GTG CTG CCT GCT GCC TCA G) (SEQ ID NO: 9). Primers for the K2383R mutation were 5'-d(CTG AGG CAG CAG GCA AGA CAG ATT TGC TAT GGG ATC A)) (SEQ ID NO: 10) and 5'-d(TGA TCC CAT AGC AAA TCT GTC TTG CCT GCT GCC TCA G)) (SEQ ID NO: 11). Primers for the K2575A/K2577A mutation were 5'-d(GTC TGT GAA ATT GAA AGT GGC AAT AGG CGC CAG CTG GGG AGA GC)) (SEQ ID NO: 12) and 5'-d (GCT CTC CCC AGC TGG CGC CTA TTG CCA CTG CCA CTT TCA ATT TCA CAG AC)) (SEQ ID NO: 13). The K2383A/K2575A/K2577A mutant plasmid was generated by PCR amplification of the wild type plasmid using primers for the K2575A/K2577A mutant. The K2383A/K2575A/K2577A mutant plasmid was generated by PCR amplification of the K2383A mutant plasmid using primers for the K2575A/K2577A mutant. PCR was conducted using 50 ng of plasmid and 15 pmol of each primer in a 50 μL reaction using Phusion polymerase according to manufacturer protocol. Briefly, the reaction contained the provided high fidelity buffer (10 μL), dNTPs (1 μL of 10 mM solution), both primers (1 μL for each, 15 μM solution), the parental plasmid (50 ng, 1 μL), Phusion polymerase (1 unit, 0.5 μL), and H$_2$O (35.5 μL). PCR was conducted with 95° C. initial denaturing (30 s), followed by 18 cycles of 95° C. denaturing (30 s), 55° C. annealing (1 min), 72° C. extension (5 min). Parental plasmid was digested by addition of Dpn1 (1 μL, 20 units) at 37° C. for 4 h. An aliquot (2 μL) of this mixture was transformed into DH5-α cells (40 μL) by incubation on ice (30 min), heat shock at 42° C. (30 s), and incubation on ice (5 min). SOC medium (200 μL) was added and outgrowth was conducted at 37° C. for 1 h with 250 rpm shaking. A portion (100 μL) of the transformed cells was plated on an LB plate with ampicillin (100 μg/mL). Plates were grown for 16 h at 37° C. A single colony was picked and resuspended in LB media (5 mL) with ampicillin (100 μg/mL) and grown for 16 h at 37° C. Plasmids were isolated by Mini prep according to the manufacturer protocol and sequenced to confirm mutagenesis. The mutant proteins were expressed and purified in the same fashion as the wild type. See Hogg et al., 2011; Malaby et al., 2017.

1.4.9. UPLC-MS/MS analysis of Pol θ modification by pC4-AP. A solution of Pol θ (100 μL, 10 μM) was mixed with H$_2$O (700 μL), 10× reaction buffer (100 μL, 500 mM HEPES pH 7.5, 200 mM KCl, 10 mM EDTA), and 1 (100 μL, 100 μM) and incubated at room temperature for 30 min. The reaction mixture was concentrated by centrifugation using an Amicon 10K centrifugal filter. To prevent loss of protein, the centrifugal filter was blocked with Pol θ prior to addition of the sample. Blocking was conducted by adding Pol θ (500 μL, 1 μM,) followed by centrifugation (13,000 g, 5 min, 4° C.) and removal of the supernatant. Following blocking of the membrane filter, half of the sample (500 μL) was added to the Amicon centrifugal filter, and centrifugation was carried out (13,000 g, 5 min, 4° C.). The remainder of the sample was added and centrifugation was repeated. The sample was then washed twice with 400 μL of reaction buffer (50 mM HEPES pH 7.5, 20 mM KCl, 1 mM EDTA) and concentrated by centrifugation in the Amicon centrifugal filter to 100 μL. Trypsin/Lys-C mix was reconstituted in the resuspension buffer provided by the manufacturer (20 μL) and added (2 μg, 2 μL) to the sample, which was incubated at 37° C. for 4 h. The digestion mixture was concentrated in a Speed Vac concentrator to 40 μL and a portion (10 μL) was analyzed by UPLC-MS/MS using an ACQUITY UPLC HSS T3 Column (100 Å, 1.8 μm, 2.1 mm×100 mm). The flow rate was 0.3 mL/min running a gradient from 85:5:10 water:acetonitrile:1% formic acid to 50:40:10 water:acetonitrile:1% formic acid over 35 min. The MS conditions were as follows. Acquisition Mode=Positive Polarity, Resolution Scan Mode; Scan type=MSe (alternating MS and pseudo MS/MS scans with ramping collision voltage); Scan time=0.5 sec/scan; Acquired Mass Range (MS)=160-3000; MSe Collision Energy Ramp=15-45 V across MSe scan; Cone Voltage=40 V; Capillary Voltage=3.0 kV; Extraction voltage=4 V; Source temp.=130° C.; Desolvation temp.=400° C.; Desolvation gas flow=400 L/h.

1.4.10. Schiff base trapping experiments. A solution of Pol θ (wild type, K2383A, K2383R, K2383A/K2575A/ K2577A, K2575A/K2577A, 250 nM) and 3'-$^{32}$P-3 (50 nM) was incubated in reaction buffer (50 mM HEPES pH 7.5, 20 mM KCl, 1 mM EDTA, and 1 mM β-mercaptoethanol) at 37° C. for 15 s. NaBH$_4$ (2.5 mM) was added and the solution was incubated at 37° C. for 1 h. In a typical experiment, a 10× solution of 3'-$^{32}$P-3 (500 nM) in 1× phosphate buffered saline (10 mM sodium phosphate 100 mM NaCl, pH 7.2) was prepared by photolysis (350 nm, 10 min). The 10× solution of 3'-$^{32}$P-3 (2 μL) was added to a solution of H$_2$O (12 µL) and 10× reaction buffer (2 µL). A 10× solution (2 µL) of Pol θ in storage buffer (20 mM Tris HCl pH 7, 300 mM NaCl, 10% glycerol, 5 mM BME) was added, and the reaction was incubated at 37° C. for 15 s. A solution of $NaBH_4$ (25 mM) was prepared in $H_2O$ and added (2 µL) to each reaction. Reactions were incubated at 37° C. for 1 h and then quenched by addition of 5 µL of 5×SDS loading buffer (200 mM Tris HCl pH 8, 5% SDS, 40% glycerol). Samples were resolved by SDS-PAGE (5% stacking, 10% resolving) run for approximately 40 min at 190 V. The gel was exposed to phosphor storage cassette and imaged by phosphorimaging.

1.4.11. Fluorescence anisotropy measurements. Anisotropy measurements were conducted using a solution of dichloro diphenyl fluorescein-labeled ternary complex 6 (1 nM) and Pol θ (varying concentrations) in a reaction buffer (50 mM HEPES pH 7.5, 20 mM KCl, 1 mM EDTA, and 1 mM β-mercaptoethanol). Samples also contained 10% Pol θ storage buffer (20 mM Tris HCl pH 7, 300 mM NaCl, 10% glycerol, 5 mM BME) by volume. In a typical experiment, a sample (300 µL) was prepared by mixing Pol θ (30 µL, 2 µM) in storage buffer with 10× reaction buffer (30 µL), 6 (30 µL, 10 nM), and $H_2O$ (210 µL). The concentration of Pol θ in this solution, termed solution A, is 200 nM. Samples containing varying concentrations of Pol θ were prepared by serial dilution with solution B. Solution B (10 mL) was prepared by mixing $H_2O$ (7.95 mL) with 10× reaction buffer (1 mL), Pol θ storage buffer (1 mL), and 6 (200 nM, 50 µL). By mixing solution A (150 µL) with solution B (150 µL), the concentration of Pol θ was decreased to 100 nM, while the concentration of 6, reaction buffer, and storage buffer remained unchanged. An aliquot (150 µL) of this new solution was then mixed with solution B (150 µL) to prepare a new solution containing 50 nM Pol θ. Serial dilutions were repeated such that, samples contained Pol θ concentrations of 200, 100, 50, 25, 12.5, 6.25, 3.13, 1.57 nM for wild type Pol θ; 300, 150, 75, 37.5, 18.75, 9.38, 4.69, 2.34, 1.17 nM for K2383A and K2383R; 100, 50, 25, 12.5, 6.25, 3.13, 1.57 nM for K2575A/K2577A; and 200, 100, 75, 50, 37.5, 25, 12.5, 6.25 nM for K2575A/K2577A/K2383A. Samples were incubated at 25° C. for 1 h and fluorescence anisotropy (A) was measured using a portion (125 µL) of each sample with PMT voltage of 800 mV, 8 nm slit width, and 535 nm excitation and 556 nm emission. Fluorescence anisotropy was measured for 6 in the absence of polymerase ($A_0$), and the change in anisotropy ($A-A_0$) was calculated for each sample and plotted against the concentration of Pol θ. The data were fit to the Hill equation $A=A_{max}([enzyme]^n/K_d^n+n)$ where n is the Hill coefficient using Origin 7.0.

1.4.12. Inhibitor screening. Pol θ was added to the wells of a 96-well fluorescence spectrometer plate containing a solution of a different putative inhibitors in Pol θ reaction buffer and the mixtures were pre-incubated for 25 min at room temperature. The pre-incubation mixtures were subsequently diluted with a solution containing DNA substrate and nucleotide triphosphates in Pol θ reaction buffer and fluorescence was monitored for approximately 100 min.

1.4.13. Inhibition of Pol θ studied by fluorescence as a function of concentration of specific inhibitors. Pol θ was added to the wells of a 96-well fluorescence spectrometer plate. Inhibitors were transferred to the wells containing Pol θ and incubated for 20 min. To determine the polymerase activity of enzyme in the presence of each inhibitor, solutions of DNA and nucleotide triphosphates were also added. The plates were placed immediately in the microtiter plate reader and the measurements started.

1.4.14. Pol θ inhibition as a function of preincubation time via fluorescence spectroscopy. Pol θ was added to five wells of a 96-well format microtiter plate. The inhibitor solution was added to the first well and preincubated for 10 min. At this time, the same portion of inhibitor was added to the second well. Equal amounts of inhibitor were added to subsequent wells after an additional 10, 20, and 30 min. Once the inhibitor was added to the fifth well, solutions of DNA and nucleotide triphosphates were added and the fluorescence measurement was started immediately.

1.4.15. Pol θ inhibition as a function of preincubation time via denaturing PAGE. Pol θ was pre-incubated with inhibitor in 1×Pol β reaction buffer at room temperature. Aliquots were withdrawn at the appropriate time intervals depending on the concentration of inhibitor, and added to DNA and nucleotide triphosphates. Aliquots were removed from the individual reactions at appropriate times. The aliquots were kept at −78° C. until analysis by denaturing PAGE.

1.4.16. Effect of dialysis on inactivated Pol θ. Pol θ was pre-incubated in the absence or presence of inhibitor for 30 min at room temperature. The Pol θ activity of each sample was immediately measured by adding to DNA and nucleotide triphosphates. Aliquots were removed from the individual reactions at appropriate times. The aliquots were kept at −78° C. until analysis by denaturing PAGE. Aliquots were dialyzed in reaction buffer containing glycerol for 24 h. The remaining activity of the enzyme was measured as described above.

1.4.17. Cell culture. HeLa cells were maintained in Dulbecco's Modified Eagle's Medium (DMEM), supplemented with 10% fetal bovine serum (FBS), 100 U $mL^{-1}$ of penicillin and 100 µg $mL^{-1}$ of streptomycin at 37° C. in a humidified incubator at 5% CO2. The adherent cultures were grown as a monolayer and passaged once after 3-4 days by trypsinizing with 0.25% Trypsin-EDTA. At 90% confluency, there are around $1.5 \times 10^7$ cells in one dish of 150 mm×25 mm.

1.4.18. Cell viability assay. Approximately $10^6$ HeLa cells were plated in each well of a 6 well culture plate (well size; 35 mm×18 mm) in DMEM containing 10% FBS and kept for 24 h at 37° C. in a CO2 incubator. After the indicated time, the medium was removed from the cell culture by aspiration, and washed once with PBS. Cells were then damaged by treatment with either bleomycin sulfate in DMSO, hydrogen peroxide, or $^{137}Cs$ in the presence or absence of (pro)inhibitor. Damaged cells were then incubated for 2 h at 37° C. in a CO2 incubator. For cells treated with bleomycin or hydrogen peroxide, the medium was then subsequently replaced with fresh DMEM-FBS and incubation was continued for an additional 1 or 2 h at 37° C. in a $CO_2$ incubator. After the indicated time, cells were trypsinized with 0.25% w/v Trypsin-EDTA and the cell suspension was prepared in phosphate buffered saline (PBS). A portion of the cell suspension was thoroughly mixed with a 0.4% solution of trypan blue in PBS, and placed on a counting to count the % of live cells using a TC20 automated cell counter. A control experiment without damage was carried out in parallel.

1.4.19. Clonogenic assay for cell survival. HeLa cells ($2 \times 10^5$) were seeded in each well of a 24 well culture plate (well size; 15.5 mm×18 mm) in 1 mL Dulbecco's Modified Eagle Medium (DMEM) growth medium supplemented with 10% FBS. After overnight incubation at 37° C. in a humidified atmosphere of 5% $CO_2$, cells were subjected to the appropriate DNA damaging conditions (or controls) in the presence or absence of (pro)inhibitor. For experiments involving recovery after DNA damage treatment, the medium was replaced after 2 h with fresh medium with or without (pro)inhibitor and incubation continued for 2-8 h. The growth medium was then removed from each well and the cells were washed with PBS. The cells were trypsinized with 0.25% w/v Trypsin-EDTA and the cell suspension was prepared in PBS. The single cell suspensions were collected in tubes and counted. Stock solutions of single cell suspensions were seeded in 6 well plates (well size; 35 mm×18 mm) in 10% DMEM-FBS. The plates were incubated in humidified atmosphere with 5% $CO_2$ for 7 days. After 7 days, the growth medium was discarded and the attached cells were treated with 0.2% w/v crystal violet solution. The excess dye was washed with water and the colonies were counted under a stereomicroscope. Plating efficiencies (PE) and survival fractions (SF) were calculated as follows: PE=number of colonies÷number of cells seeded; SF=PE÷PE (control).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Wu, W.-J.; Yang, W.; Tsai, M.-D. Nature Rev. Chem. 2017, 1, 0068.

Greenberg, M. M. Acc. Chem. Res. 2014, 47, 646-655.

Matsumoto, Y.; Kim, K. Science 1995, 269, 699-702.

Garcia-Diaz, M.; Bebenek, K.; Kunkel, T. A.; Blanco, L. J. Biol. Chem. 2001, 276, 34659-34663.

Bebenek, K.; Tissier, A.; Frank, E. G.; McDonald, J. P.; Prasad, R.; Wilson, S. H.; Woodgate, R.; Kunkel, T. A. Science 2001, 291, 2156.

Prasad, R.; Longley, M. J.; Sharief, F. S.; Hou, E. W.; Copeland, W. C.; Wilson, S. H. Nucleic Acids Res. 2009, 37, 1868-1877.

Prasad, R.; Poltoratsky, V.; Hou, E. W.; Wilson, S. H. Nucleic Acids Res. 2016, 44, 10824-10833.

Longley, M. J.; Prasad, R.; Srivastava, D. K.; Wilson, S. H.; Copeland, W. C. Proc. Nat. Acad. Sci. USA 1998, 95, 12244-12248.

Dizdaroglu, M. Mutat. Res. Rev. Mutagenesis 2015, 763, 212-245.

Dizdaroglu, M.; Jaruga, P. Free Rad. Res. 2012, 46, 382-419.

Regulus, P.; Duroux, B.; Bayle, P.-A.; Favier, A.; Cadet, J.; Ravanat, J.-L. Proc. Nat. Acad. Sci. USA 2007, 104, 14032-14037.

Burger, R. M. Chem. Rev. 1998, 98, 1153-1169.

Rabow, L. E.; Stubbe, J.; Kozarich, J. W. J. Am. Chem. Soc. 1990, 112, 3196-3203.

Guan, L.; Greenberg, M. M. J. Am. Chem. Soc. 2010, 132, 50045005.

Jacobs, A. C.; Kreller, C. R.; Greenberg, M. M. Biochemistry 2011, 50, 136-143.

Stevens, A. J.; Guan, L.; Bebenek, K.; Kunkel, T. A.; Greenberg, M. M. Biochemistry 2013, 52, 975-983.

Yousefzadeh, M. J.; Wyatt, D. W.; Takata, K.-i.; Mu, Y.; Hensley, S. C.; Tomida, J.; Bylund, G. O.; Doublié, S.; Johansson, E.; Ramsden, D. A.; McBride, K. M.; Wood, R. D. PLoS Genet. 2014, 10, e1004654.

Goff, J. P.; Shields, D. S.; Seki, M.; Choi, S.; Epperly, M. W.; Dixon, T.; Wang, H.; Bakkenist, C. J.; Dertinger, S. D.; Torous, D. K.; Wittschieben, J.; Wood, R. D.; Greenberger, J. S. Radiat. Res. 2009, 172, 165-174.

Higgins, G. S.; Boulton, S. J. Science 2018, 359, 1217.

Ceccaldi, R.; Liu, J. C.; Amunugama, R.; Hajdu, I.; Primack, B.; Petalcorin, M. I. R.; O'Connor, K. W.; Konstantinopoulos, P. A.; Elledge, S. J.; Boulton, S. J.; Yusufzai, T.; D'Andrea, A. D. Nature 2015, 518, 258-262.

Wood, R. D.; Doublie, S. DNA Repair 2016, 44, 22-32.

Yoshimura, M.; Kohzaki, M.; Nakamura, J.; Asagoshi, K.; Sonoda, E.; Hou, E.; Prasad, R.; Wilson, S. H.; Tano, K.; Yasui, A.; Lan, L.; Seki, M.; Wood, R. D.; Arakawa, H.; Buerstedde, J.-M.; Hochegger, H.; Okada, T.; Hiraoka, M.; Takeda, S. Mol. Cell 2006, 24, 115-125.

Yoon, J.-H.; Roy Choudhury, J.; Park, J.; Prakash, S.; Prakash, L. J. Biol. Chem. 2014, 289, 13177-13185.

Prasad, R.; Bebenek, K.; Hou, E.; Shock, D. D.; Beard, W. A.; Woodgate, R.; Kunkel, T. A.; Wilson, S. H. J. Biol. Chem. 2003, 278, 2964929654.

Prasad, R.; Shock, D. D.; Beard, W. A.; Wilson, S. H. J. Biol. Chem. 2010, 285, 40479-40488.

Zahn, K. E.; Averill, A. M.; Aller, P.; Wood, R. D.; Doublie, S. Nat. Struct. Mol. Biol. 2015, 22, 304-311.

Prasad, R.; Beard, W. A.; Chyan, J. Y.; Maciejewski, M. W.; Mullen, G. P.; Wilson, S. H. J. Biol. Chem. 1998, 273, 11121-11126.

Miropolskaya, N.; Petushkov, I; Kulbachinskiy, A.; Makarova, A. V. Sci. Rep. 2017, 7, 10194.

Laverty, D. J.; Greenberg, M. M. Biochemistry 2017, 56, 6726-6733.

Prasad, R.; Batra, V. K.; Yang, X. P.; Krahn, J. M.; Pedersen, L. C.; Beard, W. A.; Wilson, S. H. DNA Repair 2005, 4, 1347-1357.

Williams, S. D.; David, S. S. Biochemistry 1999, 38, 15417-15424.

Belousova, E. A.; Lavrik, O. I. DNA Repair 2015, 29, 112-126.

Tahara, Y.-k.; Auld, D.; Ji, D.; Beharry, A. A.; Kietrys, A. M.; Wilson, D. L.; Jimenez, M.; King, D.; Nguyen, Z.; Kool, E. T. J. Am. Chem. Soc. 2018, 140, 2105-2114.

Zafar, M. K.; Eoff, R. L. Chem. Res. Toxicol. 2017, 30, 1942-1955.

Gowda, A. S. P.; Suo, Z.; Sprat, T. E. Chem. Res. Toxicol. 2017, 30, 715-725.

Paul, R.; Banerjee, S.; Greenberg, M. M. ACS Chem. Biol. 2017, 12, 1576-1583.

Donley, N.; Jaruga, P.; Coskun, E.; Dizdaroglu, M.; McCullough, A. K.; Lloyd, R. S. ACS Chem. Biol. 2015, 10, 2334-2343.

Zafar, M. K.; Maddukuri, L.; Ketkar, A.; Penthala, N. R.; Reed, M. R.; Eddy, S.; Crooks, P. A.; Eoff, R. L. Biochemistry 2018, 57, 1262-1273.

Muvarak, Nidal E.; Chowdhury, K.; Xia, L.; Robert, C.; Choi, Eun Y.; Cai, Y.; Bellani, M.; Zou, Y.; Singh, Zeba N.; Duong, Vu H.; Rutherford, T.; Nagaria, P.; Bentzen, Soren M.; Seidman, Michael M.; Baer, Maria R.; Lapidus, Rena G.; Baylin, Stephen B.; Rassool, Feyruz V. Cancer Cell 2016, 30, 637-650.

Murai, J.; Huang, S.-y. N.; Das, B. B.; Renaud, A.; Zhang, Y.; Doroshow, J. H.; Ji, J.; Takeda, S.; Pommier, Y. Cancer Res. 2012, 72, 5588.

Hogg, M.; Seki, M.; Wood, R. D.; Doublie, S.; Wallace, S. S. Lesion Bypass Activity of DNA Polymerase Theta (POLQ) Is an Intrinsic Property of the Pol Domain and Depends on Unique Sequence Inserts. J. Mol. Biol. 2011, 405, 642-652.

Malaby, A. W.; Martin, S. K.; Wood, R. D.; Doublie, S. Expression and Structural Analyses of Human DNA Polymerase θ (POLQ). Methods Enzymol. 2017, 592, 103-121.

Kim, J.; Gil, J. M.; Greenberg, M. M. Synthesis and Characterization of Oligonucleotides Containing the C4'-oxidized Abasic Site Produced by Bleomycin and Other DNA Damaging Agents. Angew. Chem., Int. Ed. 2003, 42, 5882-5885.

Sczepanski, J. T.; Wong, R. S.; McKnight, J. N.; Bowman, G. D.; Greenberg, M. M. Rapid DNA-Protein Cross-Linking and Strand Scission by an Abasic Site in a Nucleosome Core Particle. Proc. Natl. Acad. Sci. 2010, 107, 22475-22480.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for identifying a DNA polymerase theta (Pol θ) inhibitor that eliminates nucleophilicity of nucleophilic residue Lys2383 of Pol θ and inhibits or reduces both lyase and polymerase activities of Pol θ, a Pol θ inhibitor that modifies nucleophilic residue Lys2575 of Pol θ, or a Pol θ inhibitor that modifies nucleophilic residue Lys2577 of Pol θ, the method comprising:

(a) contacting Pol θ with one or more candidate Pol θ inhibitors in a Pol θ reaction buffer to form a pre-incubation mixture;
   (b) incubating the pre-incubation mixture for a period of time at room temperature;
   (c) diluting the pre-incubation mixture with a solution containing a DNA substrate and nucleotide triphosphates in the Pol θ reaction buffer;
   (d) measuring fluorescence of the diluted pre-incubation mixture for a period of time; and
   (e) identifying:
      i) a Pol θ inhibitor that eliminates nucleophilicity of nucleophilic residue Lys2383 of Pol θ and inhibits or reduces both lyase and polymerase activities of Pol θ,
      ii) a Pol θ inhibitor that modifies nucleophilic residue Lys2575 of Pol θ, or
      iii) a Pol θ inhibitor that modifies nucleophilic residue Lys2577 of Pol θ.

2. The method of claim 1, wherein the Pol θ inhibitor that eliminates nucleophilicity of nucleophilic residue Lys2383 of Pol θ does not inhibit DNA binding.

* * * * *

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial sequence
<220> FEATURE:
<223> OTHER INFORMATION: Modified peptide

<400> SEQUENCE: 1

Gln Gln Ala Lys Gln Ile Cys Tyr Gly Ile Ile Tyr Gly Met Gly Ala
1               5                   10                  15

Lys

<210> SEQ ID NO 2
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: N= abasic (AP) site

<400> SEQUENCE: 2
taatggctaa cgcttnccgt aatgcagtct                                        30

<210> SEQ ID NO 3
<211> LENGTH: 30
<212> TYPE: DNA
<213> ORGANISM: Artificial sequence
<220> FEATURE:
<223> OTHER INFORMATION: Synthetic

<400> SEQUENCE: 3
agactgcatt acggaaagcg ttagccatta                                        30

<210> SEQ ID NO 4
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: N=5'-deoxyribose-5-phosphate lyase (dRP lyase)

<400> SEQUENCE: 4
```
taatggctaa cgcaanacgt aatgcagtct                                              30

<210> SEQ ID NO 5
<211> LENGTH: 30
<212> TYPE: DNA
<213> ORGANISM: Artificial sequence
<220> FEATURE:
<223> OTHER INFORMATION: Synthetic

<400> SEQUENCE: 5
agactgcatt acgtattgcg ttagccatta                                              30

<210> SEQ ID NO 6
<211> LENGTH: 14
<212> TYPE: DNA
<213> ORGANISM: Artificial sequence
<220> FEATURE:
<223> OTHER INFORMATION: Synthetic

<400> SEQUENCE: 6
agctgcaggt ccta                                                               14

<210> SEQ ID NO 7
<211> LENGTH: 30
<212> TYPE: DNA
<213> ORGANISM: Artificial sequence
<220> FEATURE:
<223> OTHER INFORMATION: Synthetic

<400> SEQUENCE: 7
aggcctcaca tgcatttagg acctgcagct                                              30

<210> SEQ ID NO 8
<211> LENGTH: 31
<212> TYPE: DNA
<213> ORGANISM: Artificial sequence
<220> FEATURE:
<223> OTHER INFORMATION: DNA Primer

<400> SEQUENCE: 8
ctgaggcagg cacagatttg ctatgggatc a                                            31

<210> SEQ ID NO 9
<211> LENGTH: 37
<212> TYPE: DNA
<213> ORGANISM: Artificial sequence
<220> FEATURE:
<223> OTHER INFORMATION: DNA Primer

<400> SEQUENCE: 9
tgatcccata gcaaatctgt gctgcctgct gcctcag                                      37

<210> SEQ ID NO 10
<211> LENGTH: 37
<212> TYPE: DNA
<213> ORGANISM: Artificial sequence
<220> FEATURE:
<223> OTHER INFORMATION: DNA Primer

<400> SEQUENCE: 10
ctgaggcagc aggcaagaca gatttgctat gggatca                                      37

<210> SEQ ID NO 11
<211> LENGTH: 37
<212> TYPE: DNA
<213> ORGANISM: Artificial sequence

```
<220> FEATURE:
<223> OTHER INFORMATION: DNA Primer

<400> SEQUENCE: 11
tgatcccata gcaaatctgt cttgcctgct gcctcag                                37

<210> SEQ ID NO 12
<211> LENGTH: 44
<212> TYPE: DNA
<213> ORGANISM: Artificial sequence
<220> FEATURE:
<223> OTHER INFORMATION: DNA Primer

<400> SEQUENCE: 12
gtctgtgaaa ttgaaagtgg caataggcgc cagctgggga gagc                        44

<210> SEQ ID NO 13
<211> LENGTH: 50
<212> TYPE: DNA
<213> ORGANISM: Artificial sequence
<220> FEATURE:
<223> OTHER INFORMATION: DNA Primer

<400> SEQUENCE: 13
gctctcccca gctggcgcct attgccactg ccactttcaa tttcacagac                  50
```